United States Patent
Hariton et al.

(10) Patent No.: US 10,531,866 B2
(45) Date of Patent: Jan. 14, 2020

(54) TECHNIQUES FOR PROVIDING A REPLACEMENT VALVE AND TRANSSEPTAL COMMUNICATION

(71) Applicant: CARDIOVALVE LTD., Or Yehuda (IL)

(72) Inventors: Ilia Hariton, Zichron Yaackov (IL); Tal Reich, Moshav Moledet (IL); Paul Kaye, Modiin (IL)

(73) Assignee: CARDIOVALVE LTD., Yahuda (IL)

(*) Notice: Subject to any disclaimer, the term of this patent is extended or adjusted under 35 U.S.C. 154(b) by 369 days.

(21) Appl. No.: 15/433,547

(22) Filed: Feb. 15, 2017

(65) Prior Publication Data

US 2017/0231766 A1 Aug. 17, 2017

Related U.S. Application Data

(60) Provisional application No. 62/295,701, filed on Feb. 16, 2016.

(51) Int. Cl.
*A61B 17/00* (2006.01)
*A61F 2/24* (2006.01)

(52) U.S. Cl.
CPC .............. *A61B 17/0057* (2013.01); *A61B 2017/00247* (2013.01); *A61F 2/2436* (2013.01)

(58) Field of Classification Search
CPC ............... A61F 2/2412; A61B 17/0057; A61B 2017/00247; A61B 2017/0057; A61B 2017/00575; A61B 2017/00597; A61B 2017/00606

USPC ........................................................ 623/2.11
See application file for complete search history.

(56) References Cited

U.S. PATENT DOCUMENTS

| | | | |
|---|---|---|---|
| 4,261,342 A | 4/1981 | Aranguren Duo | |
| 4,423,525 A | 1/1984 | Vallana et al. | |
| 4,853,986 A | 8/1989 | Allen | |
| 4,892,541 A | 1/1990 | Alonso | |
| 5,108,420 A | 4/1992 | Marks | |
| 5,314,473 A | 5/1994 | Godin | |
| 5,405,378 A | 4/1995 | Strecker | |
| 5,443,500 A | 8/1995 | Sigwart | |
| 5,607,444 A | 3/1997 | Lam | |
| 5,607,470 A | 3/1997 | Milo | |

(Continued)

FOREIGN PATENT DOCUMENTS

| | | |
|---|---|---|
| EP | 1264582 A2 | 12/2002 |
| EP | 1768630 B1 | 1/2015 |

(Continued)

OTHER PUBLICATIONS

U.S. Appl. No. 61/283,819.

(Continued)

*Primary Examiner* — Martin T Ton
(74) *Attorney, Agent, or Firm* — Frank Gao

(57) ABSTRACT

A method is provided, comprising: (1) making a transapical puncture into a left ventricle of the heart; (2) making a transseptal fenestration in the heart; (3) delivering a prosthetic valve via the transapical puncture and implanting the prosthetic valve at a mitral valve of the heart; and (4) subsequently to delivering the prosthetic valve and making the transseptal fenestration, closing the transapical puncture. Other embodiments are also described.

101 Claims, 13 Drawing Sheets

(56) References Cited

U.S. PATENT DOCUMENTS

| | | |
|---|---|---|
| 5,647,857 A | 7/1997 | Anderson et al. |
| 5,765,682 A | 6/1998 | Bley et al. |
| 5,868,777 A | 2/1999 | Lam |
| 5,873,906 A | 2/1999 | Lau et al. |
| 5,954,766 A | 9/1999 | Zadno-Azizi et al. |
| 5,980,565 A | 11/1999 | Jayaraman |
| 6,010,530 A | 1/2000 | Goicoechea |
| 6,019,787 A | 2/2000 | Richard et al. |
| 6,042,607 A | 3/2000 | Williamson, IV et al. |
| 6,074,417 A | 6/2000 | Peredo |
| 6,113,612 A | 9/2000 | Swanson et al. |
| 6,120,534 A | 9/2000 | Ruiz |
| 6,152,937 A | 11/2000 | Peterson et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vazquez et al. |
| 6,332,893 B1 | 12/2001 | Mortier et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,602,263 B1 | 8/2003 | Swanson et al. |
| 6,616,675 B1 | 9/2003 | Evard et al. |
| 6,652,556 B1 | 11/2003 | VanTassel et al. |
| 6,669,724 B2 | 12/2003 | Park et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,733,525 B2 | 5/2004 | Yang et al. |
| 6,764,518 B2 | 7/2004 | Godin |
| 6,767,362 B2 | 7/2004 | Schreck |
| 6,797,002 B2 | 9/2004 | Spence et al. |
| 6,830,585 B1 | 12/2004 | Artof et al. |
| 6,830,638 B2 | 12/2004 | Boylan et al. |
| 6,951,571 B1 | 10/2005 | Srivastava et al. |
| 6,960,217 B2 | 11/2005 | Bolduc |
| 6,964,684 B2 | 11/2005 | Ortiz et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,101,396 B2 | 9/2006 | Artof et al. |
| 7,172,625 B2 | 2/2007 | Shu et al. |
| 7,198,646 B2 | 4/2007 | Figulla et al. |
| 7,201,772 B2 | 4/2007 | Schwammenthal et al. |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,573 B2 | 5/2008 | Gabbay |
| 7,404,824 B1 | 7/2008 | Webler et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,527,646 B2 | 5/2009 | Rahdert et al. |
| 7,582,111 B2 | 9/2009 | Krolik et al. |
| 7,585,321 B2 | 9/2009 | Cribier |
| 7,621,948 B2 | 11/2009 | Herrmann et al. |
| 7,625,403 B2 | 12/2009 | Krivoruchko |
| 7,632,302 B2 | 12/2009 | Vreeman et al. |
| 7,648,528 B2 | 1/2010 | Styrc |
| 7,682,380 B2 | 3/2010 | Thornton et al. |
| 7,708,775 B2 | 5/2010 | Rowe et al. |
| 7,717,955 B2 | 5/2010 | Lane et al. |
| 7,731,741 B2 | 6/2010 | Eidenschink |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,799,069 B2 | 9/2010 | Bailey et al. |
| 7,803,181 B2 | 9/2010 | Furst et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,947,072 B2 | 5/2011 | Yang et al. |
| 7,947,075 B2 | 5/2011 | Goetz et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,016,877 B2 | 9/2011 | Seguin et al. |
| 8,016,882 B2 | 9/2011 | Macoviak et al. |
| 8,021,420 B2 | 9/2011 | Dolan |
| 8,021,421 B2 | 9/2011 | Fogarty et al. |
| 8,029,518 B2 | 10/2011 | Goldfarb et al. |
| 8,029,557 B2 | 10/2011 | Sobino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sullivan et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde et al. |
| 8,075,611 B2 | 12/2011 | Millwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |

(56) References Cited

U.S. PATENT DOCUMENTS

| | | |
|---|---|---|
| 8,092,521 B2 | 1/2012 | Figulla et al. |
| 8,105,377 B2 | 1/2012 | Liddicoat |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,235,933 B2 | 8/2012 | Keren et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,430,934 B2 | 4/2013 | Das |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,372 B2 | 6/2013 | McNamara et al. |
| 8,474,460 B2 | 7/2013 | Barrett et al. |
| 8,500,821 B2 | 8/2013 | Sobrino-Serrano et al. |
| 8,545,544 B2 | 10/2013 | Spenser et al. |
| 8,579,964 B2 | 11/2013 | Lane et al. |
| 8,585,755 B2 | 11/2013 | Chau et al. |
| 8,591,460 B2 | 11/2013 | Wilson et al. |
| 8,628,571 B1 | 1/2014 | Hacohen et al. |
| 8,828,569 B2 | 1/2014 | Benichou et al. |
| 8,652,203 B2 | 2/2014 | Quadri et al. |
| 8,657,872 B2 | 2/2014 | Seguin |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,611 B2 | 4/2014 | Nitzan et al. |
| 8,696,742 B2 | 4/2014 | Pintor et al. |
| 8,728,155 B2 | 5/2014 | Montorfano et al. |
| 8,740,962 B2 | 6/2014 | Finch et al. |
| 8,784,472 B2 | 7/2014 | Eidenschink |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,840,664 B2 | 9/2014 | Krapetian et al. |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,882,697 B2 | 11/2014 | Celermajer et al. |
| 8,894,702 B2 | 11/2014 | Quadri et al. |
| 8,906,083 B2 | 12/2014 | Obermiller et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,375 B2 | 3/2015 | Garde et al. |
| 8,992,604 B2 | 3/2015 | Gross et al. |
| 8,998,982 B2 | 4/2015 | Richter et al. |
| 9,005,155 B2 | 4/2015 | Sugimoto |
| 9,005,273 B2 | 4/2015 | Salahieh et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich, Jr. et al. |
| 9,072,603 B2 | 7/2015 | Tuval et al. |
| 9,125,740 B2 | 9/2015 | Morriss et al. |
| 9,132,009 B2 | 9/2015 | Hacohen et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,248,014 B2 | 2/2016 | Lane et al. |
| 9,277,995 B2 | 3/2016 | Celermajer et al. |
| 9,301,836 B2 | 4/2016 | Buchbinder et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford, III et al. |
| 9,427,303 B2 | 8/2016 | Liddy et al. |
| 9,439,757 B2 | 9/2016 | Wallace et al. |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,629,715 B2 | 4/2017 | Nitzan et al. |
| 9,629,716 B2 | 4/2017 | Seguin |
| 9,649,480 B2 | 5/2017 | Sugimoto et al. |
| 9,681,948 B2 | 6/2017 | Levi et al. |
| 9,681,952 B2 | 6/2017 | Hacohen et al. |
| 9,707,382 B2 | 7/2017 | Nitzan et al. |
| 9,713,696 B2 | 7/2017 | Yacoby et al. |
| 9,717,591 B2 | 8/2017 | Chau et al. |
| 9,743,932 B2 | 8/2017 | Amplatz et al. |
| 9,763,817 B2 | 9/2017 | Roeder |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 2001/0002445 A1 | 5/2001 | Vesely |
| 2001/0021872 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0036791 A1 | 2/2003 | Philipp et al. |

(56) References Cited

U.S. PATENT DOCUMENTS

| | | |
|---|---|---|
| 2003/0060875 A1 | 3/2003 | Wittens |
| 2003/0069635 A1 | 4/2003 | Cartledge et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0039414 A1 | 2/2004 | Carley et al. |
| 2004/0143315 A1 | 2/2004 | Bruun et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0176839 A1 | 9/2004 | Huynh et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0249433 A1 | 12/2004 | Freitag |
| 2004/0260389 A1 | 12/2004 | Case et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright, Jr. et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0047297 A1 | 3/2006 | Case |
| 2006/0089627 A1 | 4/2006 | Burnett et al. |
| 2006/0111773 A1 | 5/2006 | Rittgers et al. |
| 2006/0116750 A1 | 6/2006 | Hebert et al. |
| 2006/0135964 A1 | 6/2006 | Vesely |
| 2006/0155357 A1 | 7/2006 | Melsheimer |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0225759 A1 | 9/2007 | Thommen et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St Goar et al. |
| 2008/0188929 A1 | 8/2008 | Schreck |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1* | 5/2009 | Chuter ............... A61F 2/07 623/1.26 |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quadri |
| 2009/0319037 A1 | 12/2009 | Rowe et al. |

(56) References Cited

U.S. PATENT DOCUMENTS

| | | |
|---|---|---|
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fenster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter et al. |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao et al. |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130301 A1 | 5/2012 | McNamara et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0179244 A1 | 7/2012 | Schankereli et al. |
| 2012/0197292 A1 | 8/2012 | Chin-Chen et al. |
| 2012/0265296 A1 | 10/2012 | McNamara et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0300063 A1 | 11/2012 | Majkrzak et al. |

(56) References Cited

U.S. PATENT DOCUMENTS

| | | |
|---|---|---|
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041451 A1 | 2/2013 | Patterson et al. |
| 2013/0046373 A1 | 2/2013 | Cartledge et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0261738 A1 | 10/2013 | Clague et al. |
| 2013/0281988 A1 | 10/2013 | Magnin et al. |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0148891 A1 | 5/2014 | Johnson |
| 2014/0163449 A1 | 6/2014 | Rottenberg et al. |
| 2014/0172069 A1 | 6/2014 | Roeder et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194971 A1 | 7/2014 | McNamara |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277045 A1 | 9/2014 | Fazio et al. |
| 2014/0277054 A1 | 9/2014 | McNamara et al. |
| 2014/0277358 A1 | 9/2014 | Slazas |
| 2014/0277409 A1 | 9/2014 | Bortlein et al. |
| 2014/0277418 A1 | 9/2014 | Miller |
| 2014/0277422 A1 | 9/2014 | Ratz et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0350565 A1 | 11/2014 | Yacoby et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connell et al. |
| 2015/0045880 A1 | 2/2015 | Hacohen |
| 2015/0045881 A1 | 2/2015 | Lim |
| 2015/0094802 A1 | 4/2015 | Buchbinder et al. |
| 2015/0119796 A1 | 4/2015 | Finch |
| 2015/0119970 A1 | 4/2015 | Nakayama et al. |
| 2015/0127097 A1 | 5/2015 | Neumann et al. |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0164640 A1 | 6/2015 | McLean et al. |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245908 A1 | 9/2015 | Nitzan et al. |
| 2015/0245934 A1 | 9/2015 | Lombardi et al. |
| 2015/0272730 A1 | 10/2015 | Melnick et al. |
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0335429 A1 | 11/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0022423 A1 | 1/2016 | McNamara et al. |
| 2016/0022970 A1 | 1/2016 | Forcucci et al. |
| 2016/0030169 A1 | 2/2016 | Shahriari |
| 2016/0030171 A1 | 2/2016 | Quijano et al. |
| 2016/0113766 A1 | 4/2016 | Ganesan et al. |
| 2016/0113768 A1 | 4/2016 | Ganesan et al. |
| 2016/0120550 A1 | 5/2016 | McNamara et al. |
| 2016/0125160 A1 | 5/2016 | Heneghan et al. |
| 2016/0166381 A1 | 6/2016 | Sugimoto et al. |
| 2016/0213473 A1 | 7/2016 | Hacohen et al. |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324635 A1* | 11/2016 | Vidlund ............... A61F 2/2418 |
| 2016/0324640 A1 | 11/2016 | Gifford, III et al. |
| 2016/0331526 A1 | 11/2016 | Schweich, Jr. et al. |
| 2016/0331527 A1 | 11/2016 | Vidlund et al. |
| 2016/0367368 A1 | 12/2016 | Vidlund et al. |
| 2016/0374801 A1 | 12/2016 | Jimenez et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0113026 A1 | 4/2017 | Finch |
| 2017/0128205 A1 | 5/2017 | Tamir et al. |
| 2017/0128705 A1 | 5/2017 | Forcucci et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0153689 A1 | 6/2018 | Maimon et al. |
| 2018/0177594 A1 | 6/2018 | Patel et al. |
| 2018/0296341 A1 | 10/2018 | Noe et al. |

FOREIGN PATENT DOCUMENTS

| | | |
|---|---|---|
| WO | 98/43557 A1 | 10/1998 |
| WO | 99/30647 A1 | 6/1999 |
| WO | 00/47139 A1 | 8/2000 |
| WO | 01/62189 A1 | 8/2001 |
| WO | 01/87190 A2 | 11/2001 |
| WO | 2005/107650 A2 | 11/2005 |

(56) References Cited

FOREIGN PATENT DOCUMENTS

| | | | |
|---|---|---|---|
| WO | 2006/007401 | A2 | 1/2006 |
| WO | 2006/054930 | A1 | 5/2006 |
| WO | 2008/013915 | A3 | 1/2008 |
| WO | 2008/103722 | A2 | 8/2008 |
| WO | 2009/033469 | A1 | 3/2009 |
| WO | 2009/053497 | A1 | 4/2009 |
| WO | 2010/006627 | A1 | 1/2010 |
| WO | 2010/037141 | A1 | 4/2010 |
| WO | 2010/057262 | A1 | 5/2010 |
| WO | 2010/073246 | A2 | 7/2010 |
| WO | 2010/081033 | A1 | 7/2010 |
| WO | 2010/121076 | A2 | 10/2010 |
| WO | 2011/025972 | A2 | 3/2011 |
| WO | 2011/069048 | A2 | 6/2011 |
| WO | 2011/106137 | A1 | 9/2011 |
| WO | 2011/111047 | A2 | 9/2011 |
| WO | 2011/137531 | A1 | 11/2011 |
| WO | 2011/143263 | A2 | 11/2011 |
| WO | 2011/154942 | A2 | 12/2011 |
| WO | 2012/011108 | A2 | 1/2012 |
| WO | 2012/036740 | A2 | 3/2012 |
| WO | 2012/048035 | A2 | 4/2012 |
| WO | 2012/127309 | A1 | 9/2012 |
| WO | 2012/177942 | A2 | 12/2012 |
| WO | 2013/021374 | A2 | 2/2013 |
| WO | 2013/021375 | A2 | 2/2013 |
| WO | 2013078497 | A1 | 6/2013 |
| WO | 2013/128436 | A1 | 9/2013 |
| WO | 2014/145338 | A1 | 9/2014 |
| WO | 2014/164364 | A1 | 10/2014 |
| WO | 2014/194178 | A1 | 12/2014 |
| WO | 2016/113743 | A1 | 7/2016 |
| WO | 2016/125160 | A1 | 8/2016 |
| WO | 2017/223486 | A1 | 12/2017 |
| WO | 2018/025260 | A1 | 2/2018 |
| WO | 2018/029680 | A1 | 2/2018 |
| WO | 2018/039631 | A1 | 3/2018 |
| WO | 2018/106837 | A1 | 6/2018 |
| WO | 2018/112429 | A1 | 6/2018 |
| WO | 2018/118717 | A1 | 6/2018 |
| WO | 2018/131042 | A1 | 7/2018 |
| WO | 2018/131043 | A1 | 7/2018 |

OTHER PUBLICATIONS

U.S. Appl. No. 61/492,449.
U.S. Appl. No. 61/515,372.
U.S. Appl. No. 61/525,281.
U.S. Appl. No. 61/537,276.
U.S. Appl. No. 61/555,160.
U.S. Appl. No. 61/588,892.
U.S. Appl. No. 62/295,701.
USPTO FOA dated Feb. 10, 2014 in connection with U.S. Appl. No. 13/033,852.
USPTO FOA dated Feb. 15, 2013 in connection with U.S. Appl. No. 12/840,463.
USPTO FOA dated Mar. 25, 2015 in connection with U.S. Appl. No. 12/840,463.
USPTO FOA dated May 23, 2014 in connection with U.S. Appl. No. 13/412,814.
USPTO FOA dated Jul. 18, 2013 in connection with U.S. Appl. No. 13/044,694.
USPTO FOA dated Jul. 23, 2013 in connection with U.S. Appl. No. 12/961,721.
USPTO NFOA dated Jan. 21, 2016 in connection with U.S. Appl. No. 14/237,264.
USPTO NFOA dated Feb. 6, 2013 in connection with U.S. Appl. No. 13/412,814.
USPTO NFOA dated May 15, 2013 in connection with U.S. Appl. No. 12/583,979.
USPTO NFOA dated May 29, 2012 in connection with U.S. Appl. No. 12/840,463.
USPTO NFOA dated Jun. 4, 2014 in connection with U.S. Appl. No. 12/840,463.
USPTO NFOA dated Jun. 17, 2014 in connection with U.S. Appl. No. 12/961,721.
USPTO NFOA dated Jun. 30, 2015 in connection with U.S. Appl. No. 14/522,987.
USPTO NFOA dated Jul. 2, 2014 in connection with U.S. Appl. No. 13/811,308.
USPTO NFOA dated Jul. 3, 2014 in connection with U.S. Appl. No. 13/033,852.
USPTO NFOA dated Aug. 2, 2013 in connection with U.S. Appl. No. 13/033,852.
USPTO NFOA dated Sep. 12, 2013 in connection with U.S. Appl. No. 13/412,814.
USPTO NFOA dated Sep. 19, 2014 in connection with U.S. Appl. No. 13/044,694.
USPTO NFOA dated Nov. 8, 2013 in connection with U.S. Appl. No. 12/840,463.
USPTO NFOA dated Nov. 23, 2012 in connection with U.S. Appl. No. 13/033,852.
USPTO NFOA dated Nov. 27, 2015 in connection with U.S. Appl. No. 14/626,267.
USPTO NFOA dated Nov. 28, 2012 in connection with U.S. Appl. No. 12/961,721.
USPTO NFOA dated Dec. 10, 2015 in connection with U.S. Appl. No. 14/237,258.
USPTO NFOA dated Dec. 31, 2012 in connection with U.S. Appl. No. 13/044,694.
USPTO NOA dated Apr. 8, 2016 in connection with U.S. Appl. No. 14/237,258.
USPTO NOA dated May 5, 2015 in connection with U.S. Appl. No. 12/840,463.
USPTO NOA dated Aug. 15, 2014 in connection with U.S. Appl. No. 13/412,814.
USPO RR dated Jan. 20, 2016 in connection with U.S. Appl. No. 14/161,921.
USPTO RR dated Feb. 3, 2014 in connection with U.S. Appl. No. 13/811,308.
USPTO RR dated Jul. 2, 2012 in connection with U.S. Appl. No. 13/033,852.
USPTO RR dated Aug. 13, 2012 in connection with U.S. Appl. No. 13/044,694.
USPTO RR dated Aug. 14, 2012 in connection with U.S. Appl. No. 12/961,721.
USPTO Suppl. NOA dated May 10, 2016 in connection with U.S. Appl. No. 14/237,258.
USPTO Suppl. NOA dated May 20, 2016 in connection with U.S. Appl. No. 14/237,258.
USPTO NFOA dated Oct. 23, 2017 in connection with U.S. Appl. No. 14/763,004.
USPTO FOA dated Jan. 17, 2018 in connection with U.S. Appl. No. 14/763,004.
USPTO NFOA dated Feb. 7, 2018 in connection with U.S. Appl. No. 15/197,069.
USPTO NFOA dated Dec. 7, 2017 in connection with U.S. Appl. No. 15/213,791.
Interview Summary dated Feb. 8, 2018 in connection with U.S. Appl. No. 15/213,791.
USPTO NFOA dated Jan. 5, 2018 in connection with U.S. Appl. No. 15/541,783.
USPTO NFOA dated Feb. 2, 2018 in connection with U.S. Appl. No. 15/329,920.
Invitation to pay additional fees dated Jan. 2, 2018; PCT/IL2017/050849.
Extended European Search Report dated Sep. 26, 2018; Appln. No. 18186784.7.
The First Chinese Office Action dated Nov. 5, 2018; Appln. No. 201680008328.5.
Invitation to pay additional fees dated Oct. 11, 2018; PCT/IL2018/050725.
USPTO NFOA dated Dec. 4, 2018 in connection with U.S. Appl. No. 16/045,059.

(56) References Cited

OTHER PUBLICATIONS

USPTO NOA dated Sep. 25, 2018 in connection with U.S. Appl. No. 15/188,507.
Extended European Search Report dated Feb. 18, 2015; Appln. 12821522.5.
Alexander S. Geha, et al; "Replacement of Degenerated Mitral and Aortic Bioprostheses Without Explantation", Ann. Thorac Surg. Jun. 2001; 72, pp. 1509-1514.
Dominique Himbert; "Mitral Regurgitation and Stenosis from Bioprosthesis and Annuloplasty Failure: Transcatheter approaches and outcomes", Cardiovascular Research Foundation, 24 pages, Oct. 28, 2013.
Frank Langer, et al; "RING plus STRING: Papillary muscle repositioning as an adjunctive repair technique for ischemic mitral regurgitation", J. Thorac Cardiovasc Surg. 133: 247-9, Jan. 2007.
Frank Langer, et al; "RING+STRING Successful Repair Technique for Ischemic Mitral Regurgitation With Severe Leaflet Tethering", Circulation 120[suppl 1]: S85-S91, Sep. 2009.
John G Webb, et al; "Transcatheter Valve-in-Valve Implantation for Failed Bioprosthetic Heart Valves", Circulation, Apr. 2010; 121: 1848-1857.
J. Jansen, et al; "Detachable shape-memory sewing ring for heart valves", Artificial Organs, 16:294-297, 1992 (an abstract).
Invitation to Pay Additional Fees; dated Jun. 12, 2014; PCT/IL2014/050087.
IPRP issued Dec. 2, 2013; PCT/IL2011/000582.
IPRP issued Sep. 11, 2012; PCT/IL2011/000231.
IPRP issued Feb. 11, 2014; PCT/IL2012/000292.
IPRP issued Feb. 11, 2014; PCT/IL2012/000293.
ISR and WO dated Dec. 5, 2011; PCT/IL11/00582.
ISR and WO dated Mar. 17, 2014; PCT/IL13/50937.
ISR and WO dated Oct. 13, 2011; PCT/IL11/00231.
ISR and WO dated Feb. 6, 2013; PCT/IL2012/000292.
ISR and WO dated Feb. 6, 2013; PCT/IL2012/000293.
ISR and WO dated Sep. 4, 2014; PCT/IL2014/050087.
ISR and WO dated Oct. 27, 2015; PCT/IL2015/050792.
An Office Action dated Jun. 6, 2018, which issued during the prosecution of UK Patent Application No. 1720803.4.
An Office Action dated Jun. 18, 2018, which issued during the prosecution of UK Patent Application No. 1800399.6.
An International Search Report and a Written Opinion both dated Jun. 20, 2018, which issued during the prosecution of Applicant's PCT/IL2018/050024.
USPTO AA dated Apr. 2, 2018 in connection with U.S. Appl. No. 14/763,004.
USPTO RR dated May 4, 2018 in connection with U.S. Appl. No. 15/872,501.
USPTO NFOA dated Jul. 26, 2018 in connection with U.S. Appl. No. 15/872,501.
USPTO NOA dated Apr. 20, 2018 in connection with U.S. Appl. No. 15/878,206.
USPTO NFOA dated Apr. 20, 2018 in connection with U.S. Appl. No. 15/886,517.
USPTO NFOA dated Aug. 9, 2018 in connection with U.S. Appl. No. 15/899,858.
USPTO NFOA dated Aug. 9, 2018 in connection with U.S. Appl. No. 15/002,403.
USPTO NFOA dated Jun. 28, 2018 in connection with U.S. Appl. No. 29/635,658.
USPTO NFOA dated Jun. 28, 2018 in connection with U.S. Appl. No. 29/635,661.
Invitation to pay additional fees dated Sep. 29, 2017 PCT/IL2017/050873.
Extended European Search Report dated Jun. 29, 2017; Appln. 11809374.9.
An International Search Report and a Written Opinion both dated May 13, 2019, which issued during the prosecution of Applicant's PCT/IL2018/051350.
An International Search Report and a Written Opinion both dated Apr. 5, 2019, which issued during the prosecution of Applicant's PCT/IL2019/050142.
An International Search Report and a Written Opinion both dated Jan. 25, 2019, which issued during the prosecution of Applicant's PCT/IL2018/051122.
An International Search Report and a Written Opinion both dated Dec. 5, 2016, which issued during the prosecution of Applicant's PCT/IL2018/050725.
An Internationai Preliminary Report on Patentability dated Feb. 12, 2019, which issued during the prosecution of Applicant's PCT/IL2017/050873.
An International Preliminary Report on Patentability dated Feb. 5, 2019, which issued during the prosecution of Applicant's PCT/IL2017/050849.
An Office Action dated Mar. 25, 2019, which issued during the prosecution of European Patent Application No. 14710060.6.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An International Search Report and a Written Opinion both dated Nov. 9, 2018, which issued during the prosecution of Applicant's PCT/IL2018/050869.

* cited by examiner

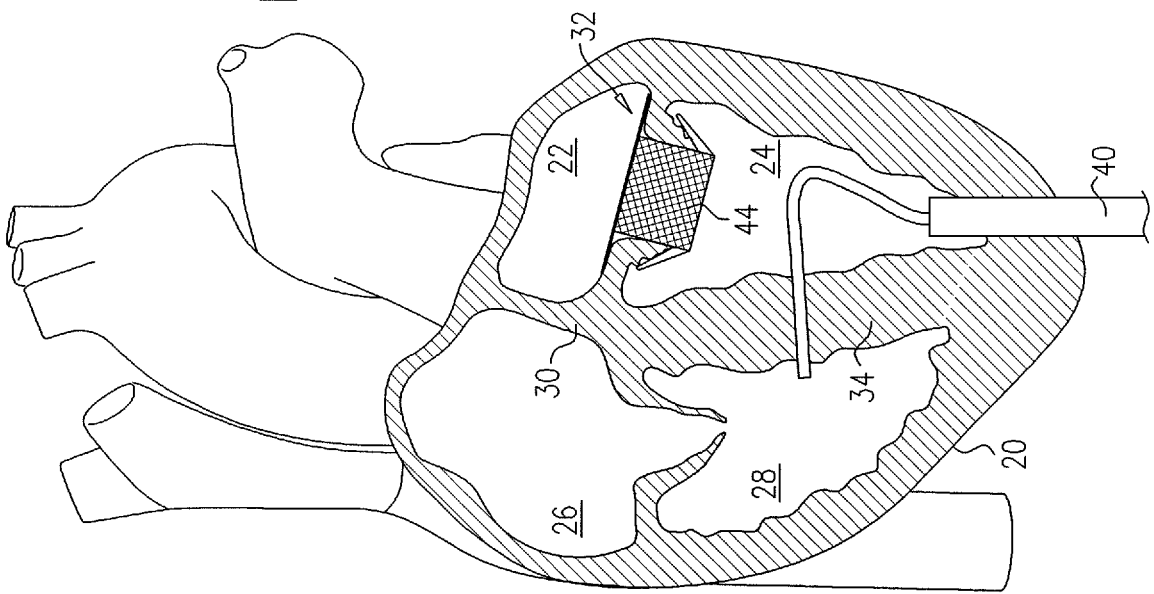
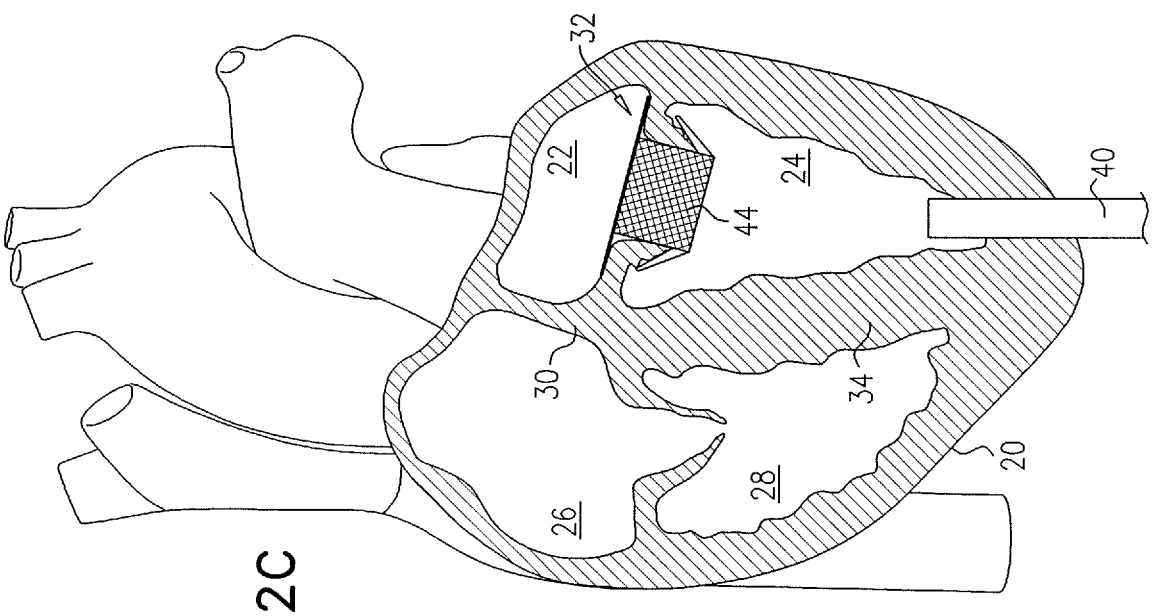

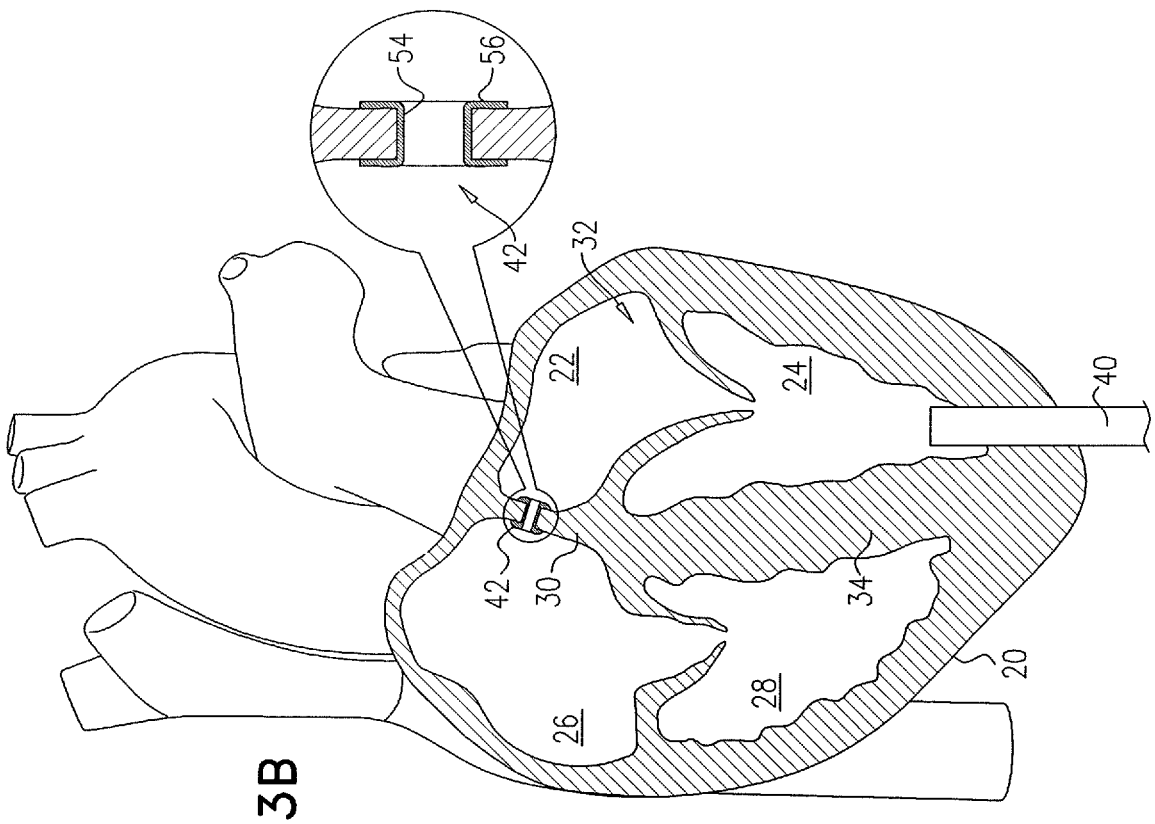
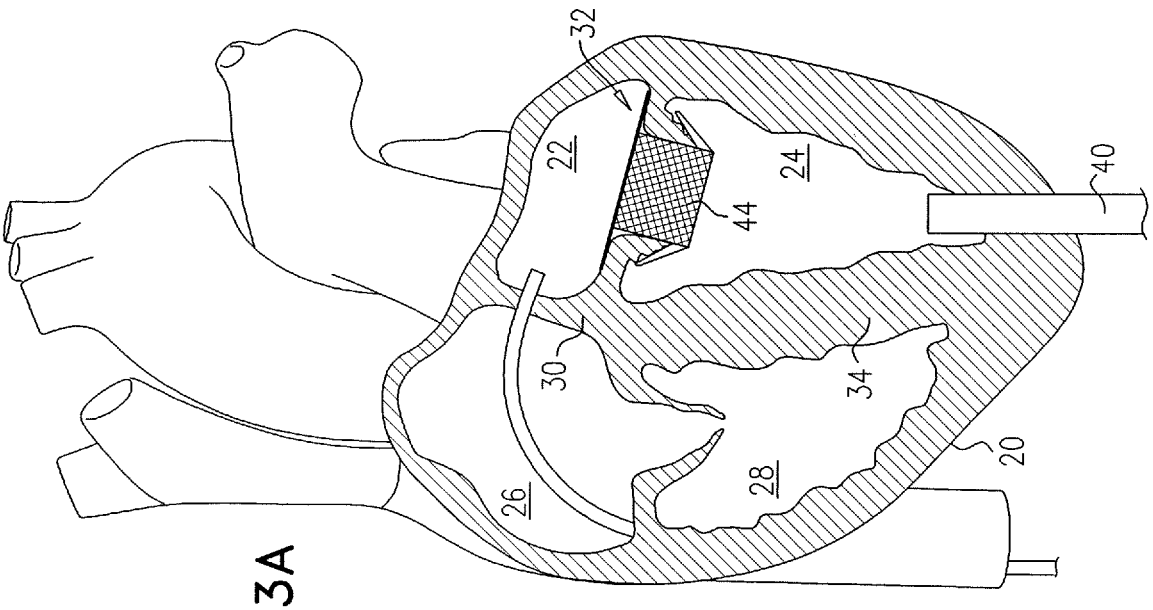

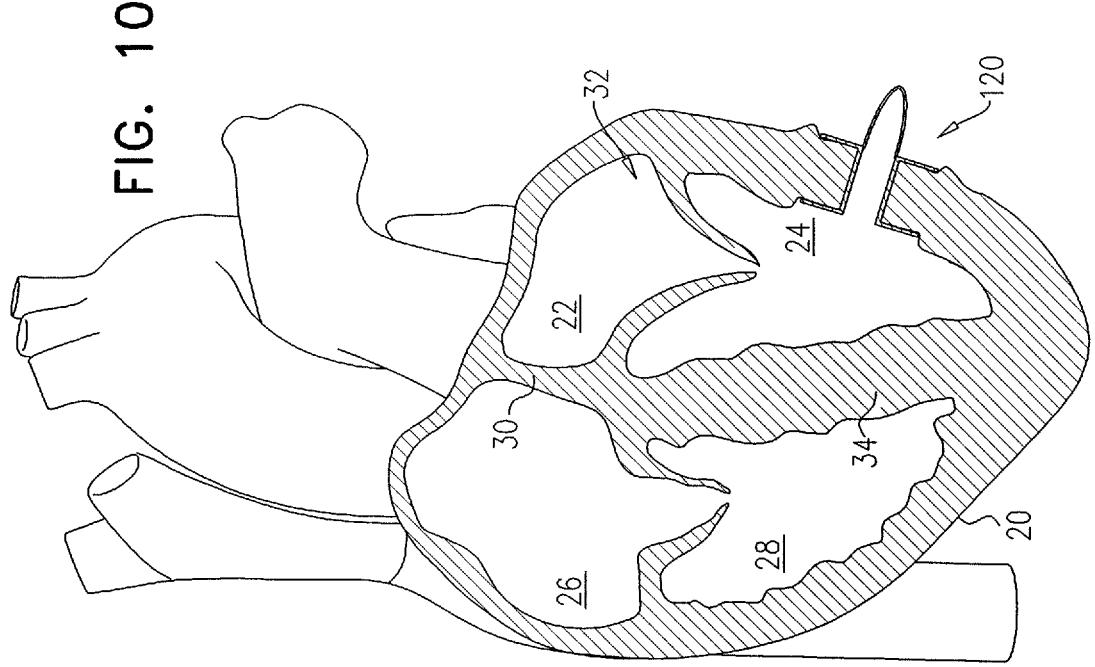
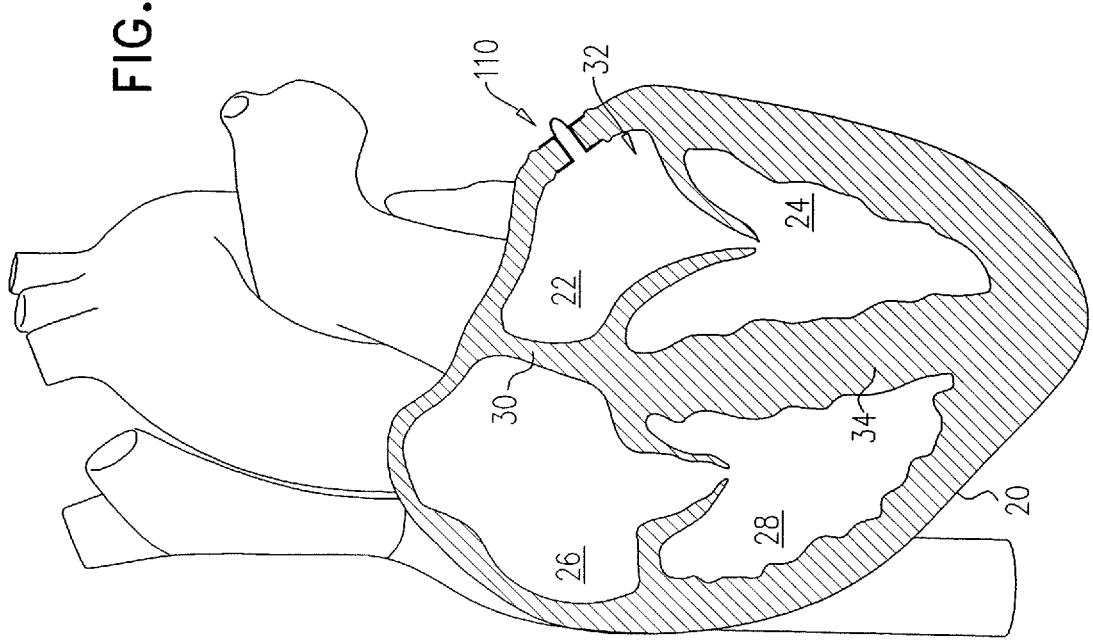

TECHNIQUES FOR PROVIDING A REPLACEMENT VALVE AND TRANSSEPTAL COMMUNICATION

CROSS-REFERENCE TO RELATED APPLICATIONS

The present application claims the benefit of U.S. Provisional application No. 62/295,701 to Hariton et al., filed Feb. 16, 2016, and entitled "Techniques for providing a replacement valve and transseptal communication," which is incorporated herein by reference.

FIELD OF THE INVENTION

Some applications of the present invention relate in general to cardiac implants. More specifically, some applications of the present invention relate to techniques for implanting cardiac implants in a complementary manner.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications, during a single medical procedure, a prosthetic valve is implanted in the heart of a subject, and a transseptal fenestration is made in the heart. For example, the implantation and fenestration may be performed via the same transapical access point (i.e., made by transapical puncture). Alternatively, the implantation or the fenestration may be performed via the transapical access point, and the other may be performed via transfemoral access. Typically, the procedure is performed on a subject that has been identified as having mitral valve regurgitation.

For some applications, the transseptal fenestration is made in the interatrial septum of the heart. For some applications, the transseptal fenestration is made in the interventricular septum of the heart.

For some applications, the transseptal fenestration is left as-is, as a transseptal shunt. For some applications, a septal device is implanted at (e.g., in) the transseptal fenestration. For some applications, the septal device is a shunt device, which is implanted at the fenestration so as to maintain patency. For some applications, the septal device is a flow-restricting device, such as a valve or a membrane, which is implanted at the fenestration so as to allow limited flow of blood between the right and left sides of the heart. For example, flow may be allowed in only one direction, and/or in response to a blood pressure difference that is greater than a threshold blood pressure difference.

For some applications, the septal device comprises a membrane or a balloon, and is implanted at the fenestration so as to facilitate temporary and reversible changes in the effective volume of the left atrium or left ventricle of the heart, e.g., without allowing mixing of blood between the right and left sides of the heart. For some applications, the septal device comprises a cell that performs a similar function. For example, the cell may slide into and out of the right side of the heart (e.g., the right atrium) in response to the blood pressure difference.

For some applications, the membrane, balloon, and/or cell is implanted in the heart wall, rather than in the septum.

There is therefore provided, in accordance with an application of the present invention, a method for use with a heart of a subject, the method including:

making a transapical puncture into a left ventricle of the heart;

making a transseptal fenestration in the heart;

delivering a prosthetic valve via the transapical puncture and implanting the prosthetic valve at a mitral valve of the heart; and subsequently to delivering the prosthetic valve and making the transseptal fenestration, closing the transapical puncture.

In an application, the subject has not been identified as suffering from heart failure, and performing the method includes performing the method on the subject that has not been identified as suffering from heart failure.

In an application, making the transseptal fenestration includes making the transseptal fenestration via the transapical puncture.

In an application, making the transseptal fenestration includes making the transseptal fenestration via a transfemoral route.

In an application, making the transseptal fenestration includes making a fenestration in the interventricular septum.

In an application, making the transseptal fenestration includes making a fenestration in the interatrial septum.

In an application, making the transseptal fenestration includes making the transseptal fenestration after implanting the prosthetic valve.

In an application, making the transseptal fenestration includes making the transseptal fenestration before implanting the prosthetic valve.

In an application, the method further includes advancing a distal end of a tube through the transapical puncture, and delivering the prosthetic valve via the transapical puncture includes delivering the prosthetic valve via the tube.

In an application, making the transseptal fenestration includes making the transseptal fenestration via the tube.

In an application, the method further includes implanting a shunt device into the transseptal fenestration.

In an application, the shunt device includes a check valve, and implanting the shunt device includes implanting the shunt device such that the check valve facilitates one-way blood flow from a chamber of the left side of the heart, via the transseptal fenestration, to a chamber of the right side of the heart.

In an application, implanting the shunt device includes implanting a shunt device that is shaped to define a lumen, and includes a membrane that regulates blood flow through the lumen.

In an application, implanting the shunt device includes implanting a shunt device that includes a membrane that (a) has (i) a closed position in which the membrane inhibits blood flow through the lumen, and (ii) an open position in which the inhibiting of the blood flow is reduced, resides in the closed position while a blood pressure difference across the membrane is lower than a threshold blood pressure difference of 4-6 mmHg (e.g., 5 mmHg), and moves from the closed position into the open position in response to the blood pressure difference exceeding the threshold blood pressure difference.

In an application, the membrane moves from the closed position into the open position in response to the blood pressure difference exceeding the threshold blood pressure difference in either direction across the membrane, and implanting the shunt device that includes the membrane includes implanting the shunt device that includes the membrane that moves from the closed position into the open position in response to the blood pressure difference exceeding the threshold blood pressure difference in either direction across the membrane.

In an application, the membrane is transected by intersecting slits, and implanting the shunt device includes implanting the shunt device that includes the membrane that is transected by intersecting slits.

In an application, the method further includes implanting at the transseptal fenestration, a balloon device that includes a balloon having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart inflates the balloon such that the balloon reversibly expands into the corresponding chamber of the right side of the heart.

In an application, the balloon is elastic, and implanting the balloon device includes implanting the balloon device such that the balloon automatically deflates in response to a reduction in the greater blood pressure in the chamber of the left side of the heart.

In an application, implanting the balloon device includes implanting the balloon such that the balloon inflates only when blood pressure in the chamber of the left side of the heart is more than 4-6 mmHg greater than blood pressure in the chamber of the right side of the heart.

In an application, implanting the balloon device includes sealing the transseptal fenestration with the balloon device.

In an application, the method further includes implanting at the transseptal fenestration, an elastic membrane that elastically expands in response to a difference in blood pressure across the membrane.

In an application, implanting the elastic membrane includes sealing the transseptal fenestration with the elastic membrane.

In an application, the method further includes implanting at the transseptal fenestration, a cell having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart increases a volume of the interior that is disposed within the corresponding chamber of the right side of the heart.

In an application, the cell includes an elastic membrane, and implanting the cell includes implanting the cell that includes the elastic membrane, such that the elastic membrane elastically expands into the chamber of the right side of the heart in response to the greater blood pressure in the chamber of the left side of the heart.

In an application, the cell is a balloon, and implanting the cell includes implanting the balloon, such that the balloon expands into the chamber of the right side of the heart in response to the greater blood pressure in the chamber of the left side of the heart.

In an application, implanting the cell includes implanting a cell that is slidably mounted in a mount, such that the mount is fixed at the transseptal fenestration, and the cell slides into the chamber of the right side of the heart in response to the greater blood pressure in the chamber of the left side of the heart.

In an application, implanting the cell includes implanting the cell such that the volume of the interior that is disposed within the corresponding chamber of the right side of the heart increases only when the blood pressure in the chamber of the left side of the heart is greater than the blood pressure in the chamber of the right side of the heart by more than a threshold difference of 4-6 mmHg.

There is further provided, in accordance with an application of the present invention, a method including for use with a heart of a subject:

identifying the subject as having mitral valve regurgitation;

during a medical procedure, in response to identifying the subject as having mitral valve regurgitation, implanting a prosthetic valve at a mitral valve site of the heart; and during the same medical procedure, implanting a shunt device at a septum of the heart.

In an application, implanting the prosthetic valve and implanting the shunt device include implanting the prosthetic valve and implanting the shunt device in the absence of an identification of the subject as having heart failure.

In an application, the septum is an interatrial septum of the heart, and implanting the shunt device at the septum includes implanting the shunt device at the interatrial septum.

In an application, the septum is an interventricular septum of the heart, and implanting the shunt device at the septum includes implanting the shunt device at the interventricular septum.

In an application, the subject is an adult subject, and the method is performed on the adult subject.

There is further provided, in accordance with an application of the present invention, a method including for use with a heart of a subject:

identifying the subject as having mitral valve regurgitation;

during a medical procedure, in response to identifying the subject as having mitral valve regurgitation, implanting a prosthetic valve at a mitral valve site of the heart; and during the same medical procedure, implanting a septal device at a septum of the heart.

In an application, implanting the prosthetic valve and implanting the septal device include implanting the prosthetic valve and implanting the septal device in the absence of an identification of the subject as having heart failure.

In an application, the septum is an interatrial septum of the heart, and implanting the septal device at the septum includes implanting the septal device at the interatrial septum.

In an application, the septum is an interventricular septum of the heart, and implanting the septal device at the septum includes implanting the septal device at the interventricular septum.

In an application, the subject is an adult subject, and the method is performed on the adult subject.

The present invention will be more fully understood from the following detailed description of applications thereof, taken together with the drawings, in which:

BRIEF DESCRIPTION OF THE DRAWINGS

FIGS. 2A-F are schematic illustrations of a method for use with heart of a subject, in accordance with some applications of the invention;

FIGS. 3A-B are schematic illustrations of a method for use with heart of a subject, in accordance with some applications of the invention;

FIGS. 9 and 10 are schematic illustrations of septal devices implanted in the heart wall, in accordance with an application of the invention.

DETAILED DESCRIPTION OF EMBODIMENTS

Figure 1A:
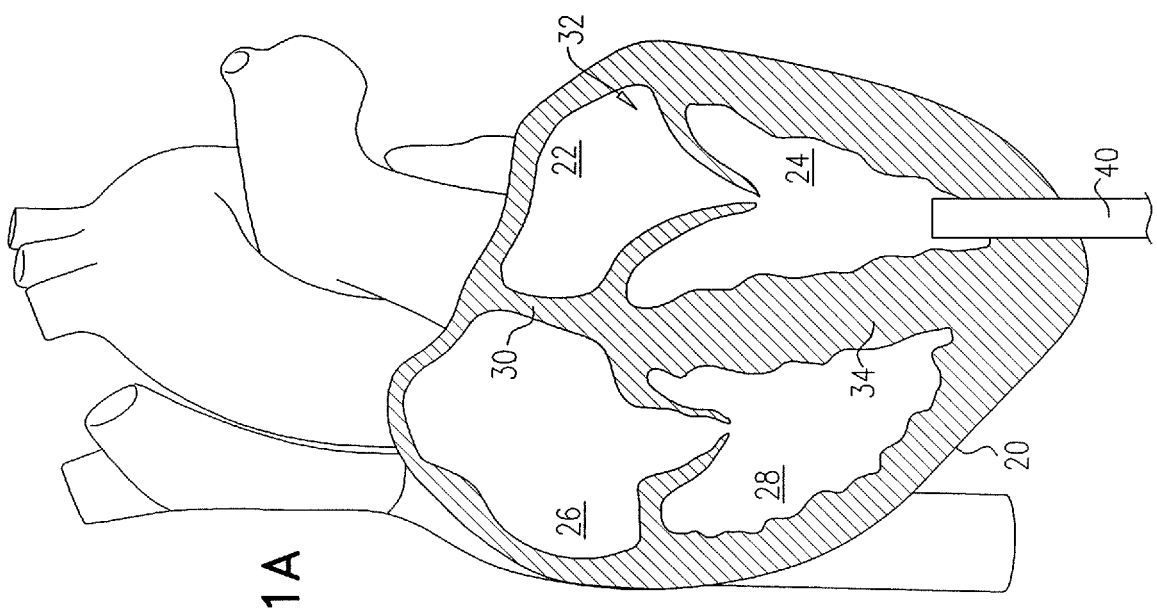
FIGS. 1A-F are schematic illustrations of a method for use with a heart of a subject, in accordance with some applications of the invention.

Reference is made to FIGS. 1A-F, which are schematic illustrations of a method for use with a heart 20 of a subject, in accordance with some applications of the invention. Heart 20 has a left atrium 22 and a left ventricle 24 (the left side of the heart), and a right atrium 26 and a right ventricle 28 (the right side of the heart).

Figure 1B:
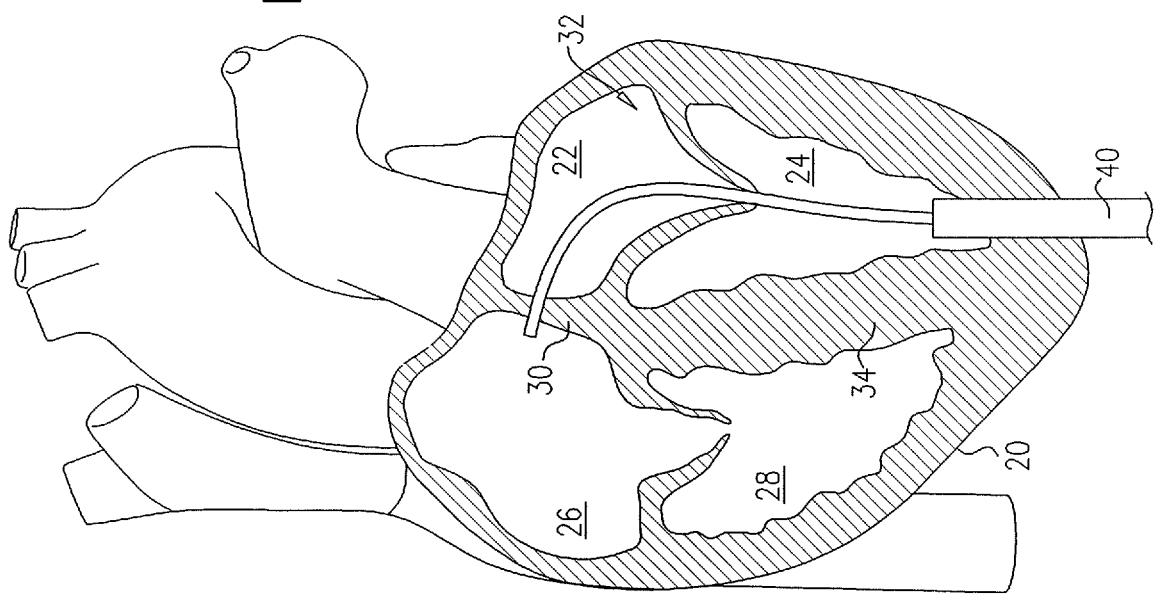
Figure 1C:
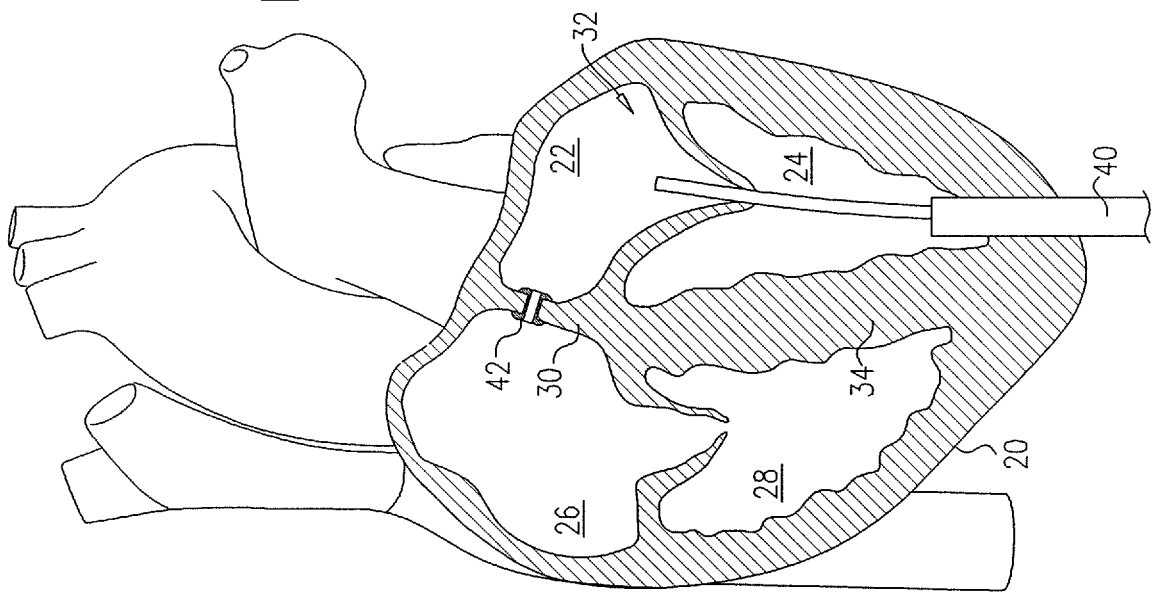
Figure 1D:
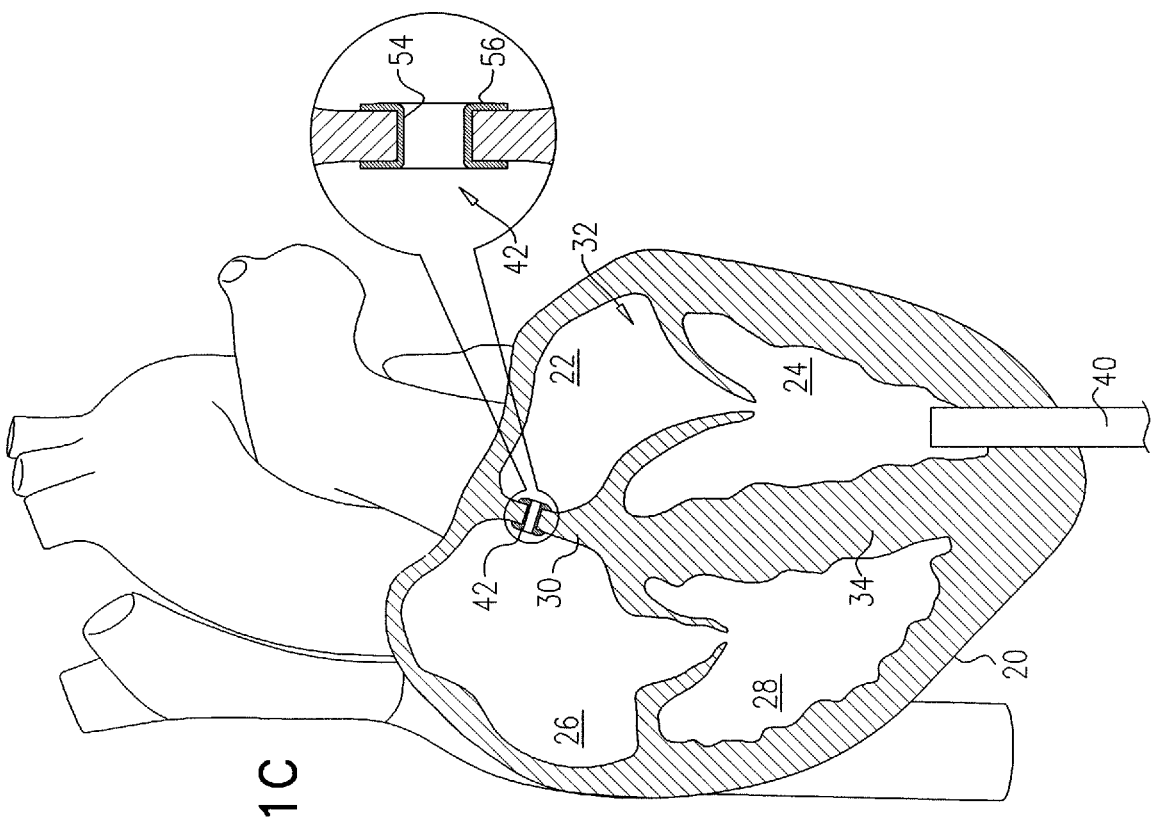
Figure 1F:
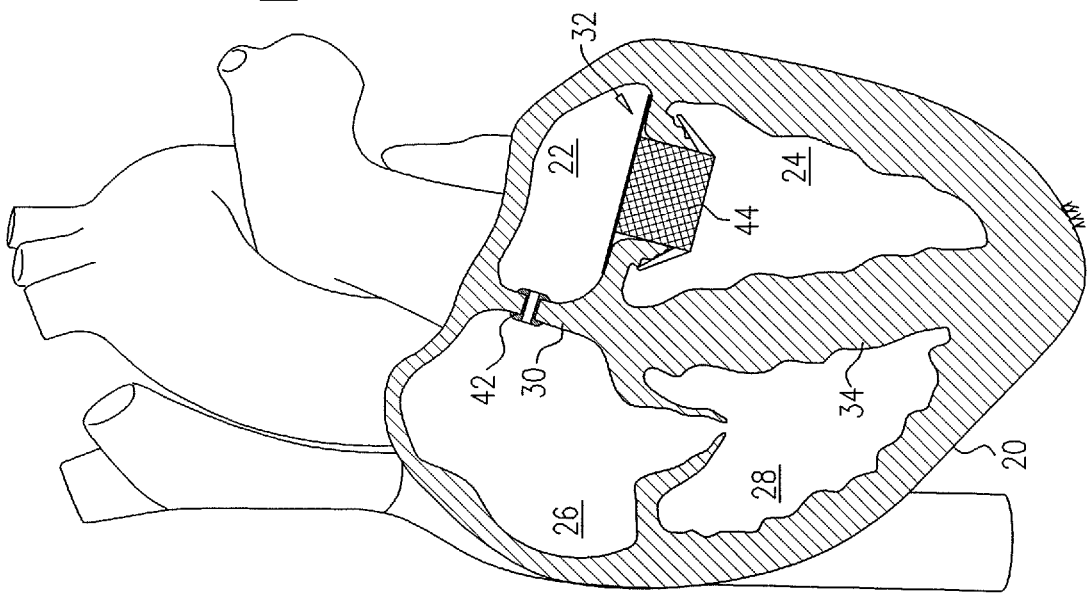
Figure 1E:
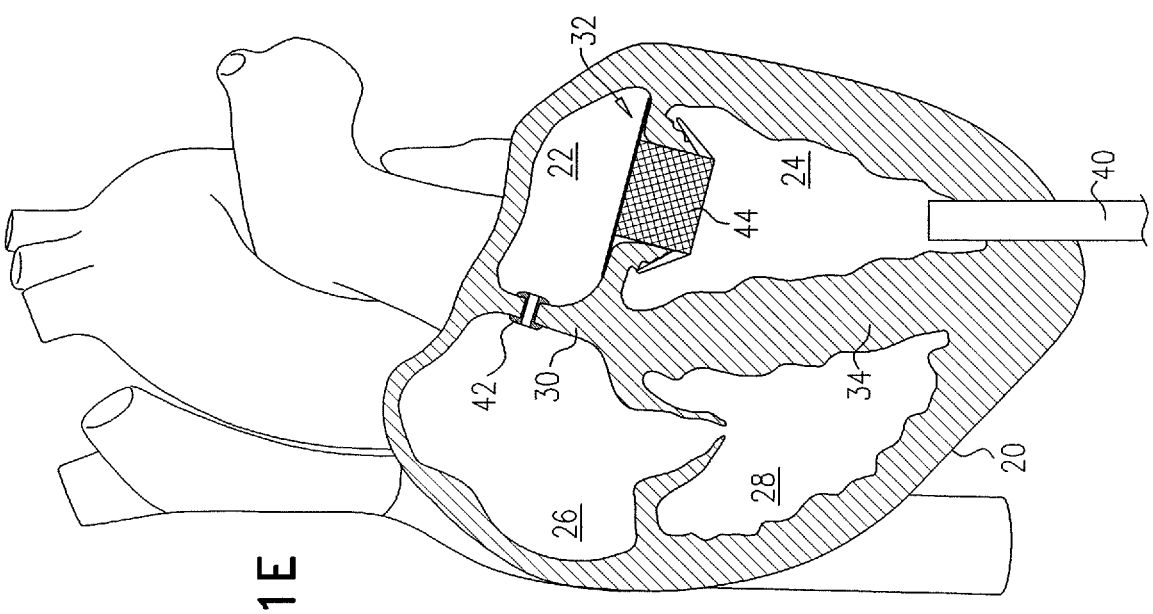
Figure 2A:
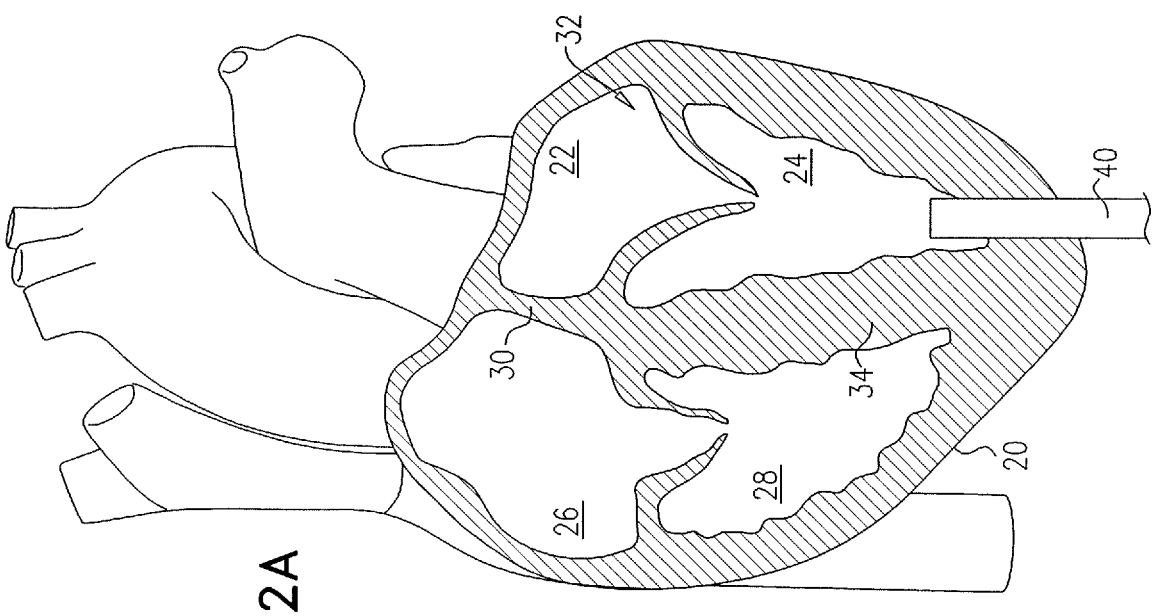
Figure 2B:
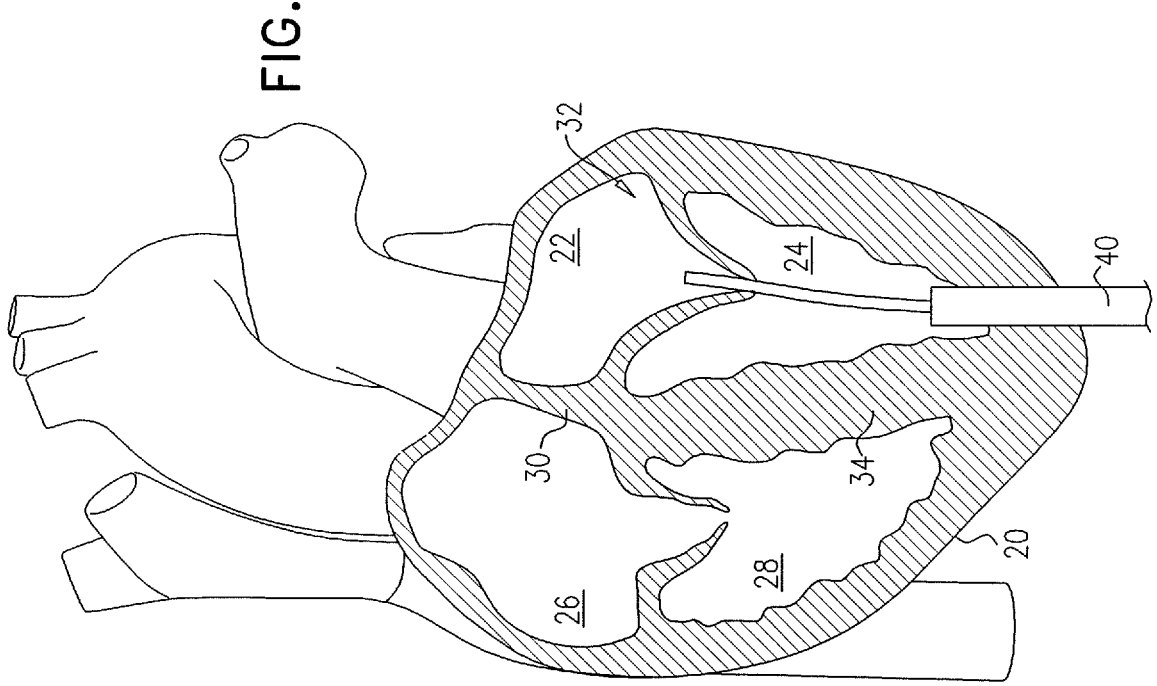
Figure 2F:
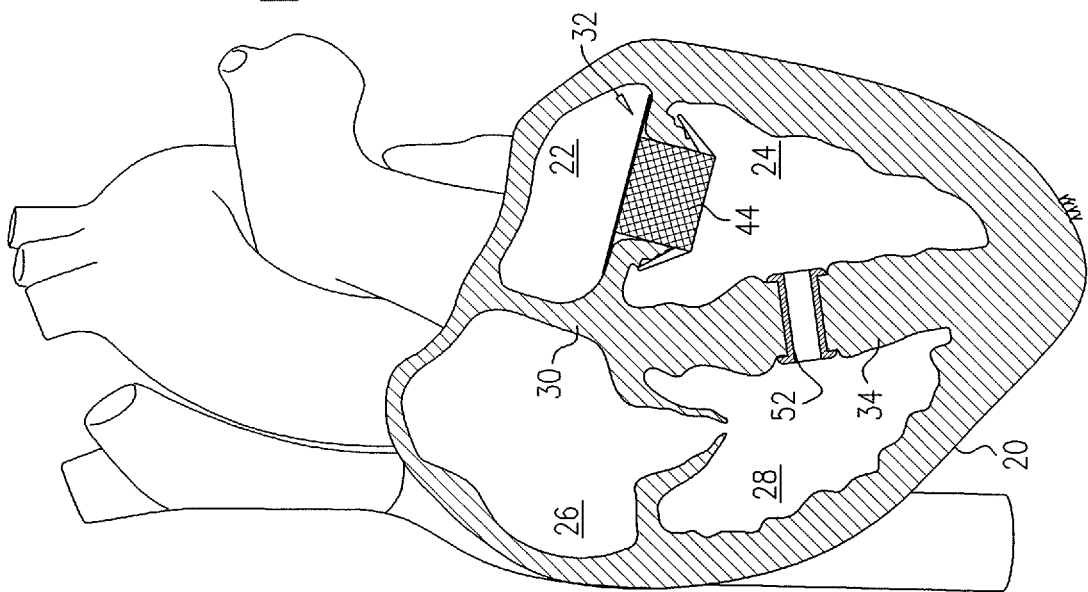
Figure 2E:
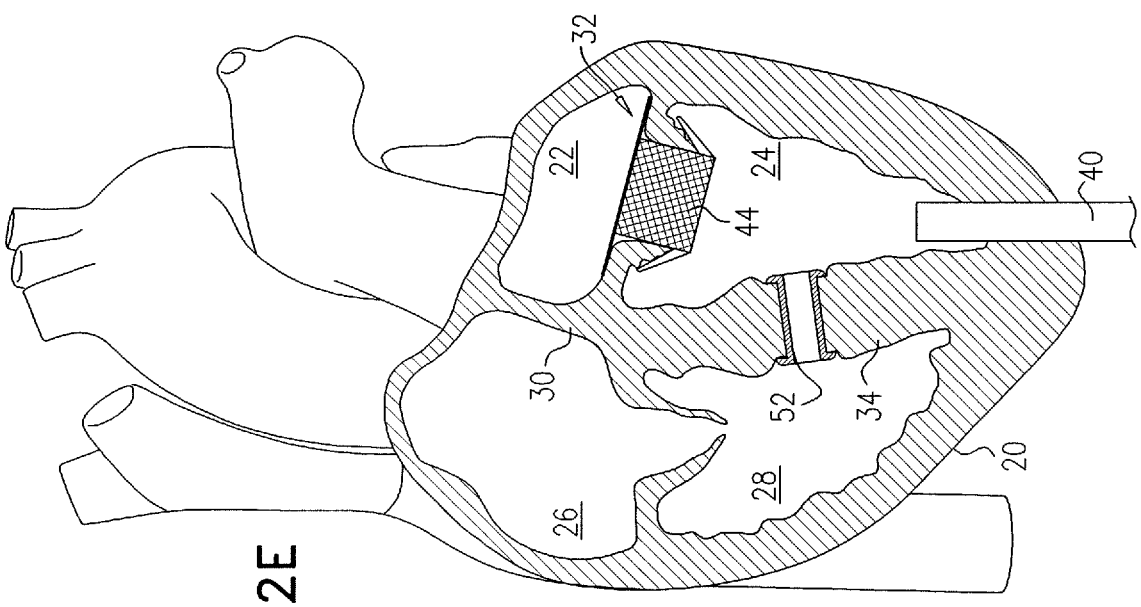

A transapical puncture is made into left ventricle 24 (FIG. 1A). For some applications, a tube 40 is introduced through the transapical puncture. Via the transapical puncture (e.g., via tube 40), a transseptal fenestration is made in interatrial septum 30 (e.g., in the fossa ovalis) (FIG. 1B). For some applications, a septal device 42 (e.g., a shunt device) is implanted at the transseptal fenestration (FIG. 1C). Subsequently, via the transapical puncture (e.g., via tube 40), a prosthetic valve 44 is delivered (FIG. 1D) and implanted at mitral valve 32 of the subject (FIG. 1E). Subsequently, the transapical puncture is closed (FIG. 1F).

Reference is made to FIGS. 2A-F, which are schematic illustrations of a method for use with heart 20 of a subject, in accordance with some applications of the invention. The method of FIGS. 2A-F is similar to that of FIGS. 1A-F, except that (i) prosthetic valve 44 is delivered and implanted prior to making the transseptal fenestration (FIGS. 2B-C), and (ii) the transseptal fenestration is made (and optionally a septal device 52, such as a shunt device, is implanted) in interventricular septum 34 (FIGS. D-E).

Reference is again made to FIGS. 1A-2F. It is to be noted that the scope of the invention includes making the transseptal fenestration in interventricular septum 34 even when making the transseptal fenestration prior to implantation of prosthetic valve 44. It is also to be noted that the scope of the invention includes implanting prosthetic valve 44 prior to making the transseptal fenestration even for applications in which the transseptal fenestration is made in the interatrial septum.

Reference is made to FIGS. 3A-B, which are schematic illustrations of a method for use with heart 20 of a subject, in accordance with some applications of the invention. The method shown in FIGS. 3A-B is identical to those described with reference to FIGS. 1A-2F hereinabove, except that the transseptal fenestration is made (and optionally, septal device 42 or 52 is implanted) via a transvenous (e.g., transfemoral) route. The transseptal fenestration (and/or the implantation of septal device 42 or 52) may be made before or after prosthetic valve 44 is implanted. FIGS. 3A-B show the transseptal fenestration in interatrial septum 30, but it is to be noted that the scope of the invention includes the transseptal fenestration being in interventricular septum 34, mutatis mutandis).

Reference is again made to FIGS. 1A-3B. For some applications, rather than via transapical puncture, prosthetic valve 44 is implanted via a transatrial puncture (i.e., a puncture through the heart wall into atrium 22). For such applications, the transseptal fenestration may be made via the transatrial puncture or via a different route.

Reference is again made to FIGS. 1A-3B. It is to be noted that prosthetic valve 44 is not delivered to mitral valve 32 via the transseptal fenestration. That is, the transseptal fenestration described herein is not itself required for delivery of the prosthetic valve.

Reference is now made to FIGS. 4-8, which are schematic illustrations of septal devices that may be implanted at the transseptal fenestration, in accordance with some applications of the invention. Hereinabove a shunt device is used as an example of devices 42 and 52. A shunt device is typically used to maintain patency of the transseptal fenestration. For example, and as shown in FIG. 2C, a shunt device may have a tubular portion 54 that is shaped to define a lumen, with flanges 56 (that are typically expandable) that engage the tissue of the septum, and retain the shunt device within the transseptal fenestration. FIGS. 4-8 are other examples of devices that may be implanted in place of device 42 or device 52, mutatis mutandis.

Figure 4:
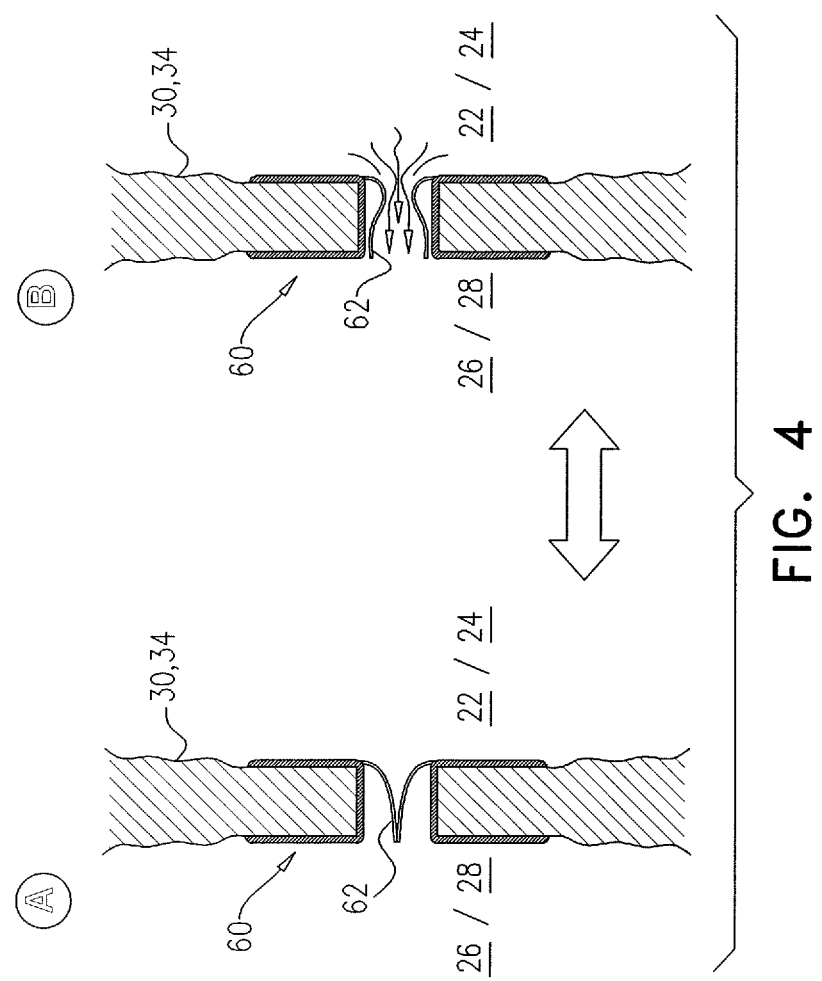
FIGS. 4, 5, 6, 7 and 8 are schematic illustrations of respective septal devices that may be implanted at the transseptal fenestration, in accordance with some applications of the invention.

FIG. 4 is a schematic illustration of a septal device 60 that is shaped to define a lumen, and comprises a check valve 62 that facilitates one-way blood flow through the lumen (and thereby through the transseptal fenestration). Device 60 is typically oriented such that the one-way blood flow is from a chamber of the left side of the heart to a chamber of the right side of the heart (e.g., from left atrium 22 to right atrium 26, or from left ventricle 24 to right ventricle 28). Check valve 62 is shown as a leaflet or duckbill valve, but it is to be understood that any suitable check valve known in the art may be used (such as, but not limited to, a ball-and-cage valve or a tilting-disc valve). For some applications (e.g., when check valve 62 is a leaflet or duckbill valve), check valve 62 thereby comprises a membrane (i.e., the leaflets or the duckbill membrane) that regulates blood flow through the lumen of the valve.

Frame A shows a state of device 60 (i.e., closed) when a blood pressure difference across the device (e.g., across valve 62) is less than a threshold blood pressure difference. That is, when blood pressure on the left side of the heart is less than a threshold amount greater than blood pressure on the right side of the heart (e.g., including if the pressure on the left side of the heart is not greater than the pressure on the right side of the heart). Frame B shows a state of device 60 (i.e., open) when the blood pressure difference is greater than the threshold blood pressure difference. For some applications, the threshold blood pressure difference for device 60 is 4-6 mmHg (e.g., 5 mmHg).

Figure 5:
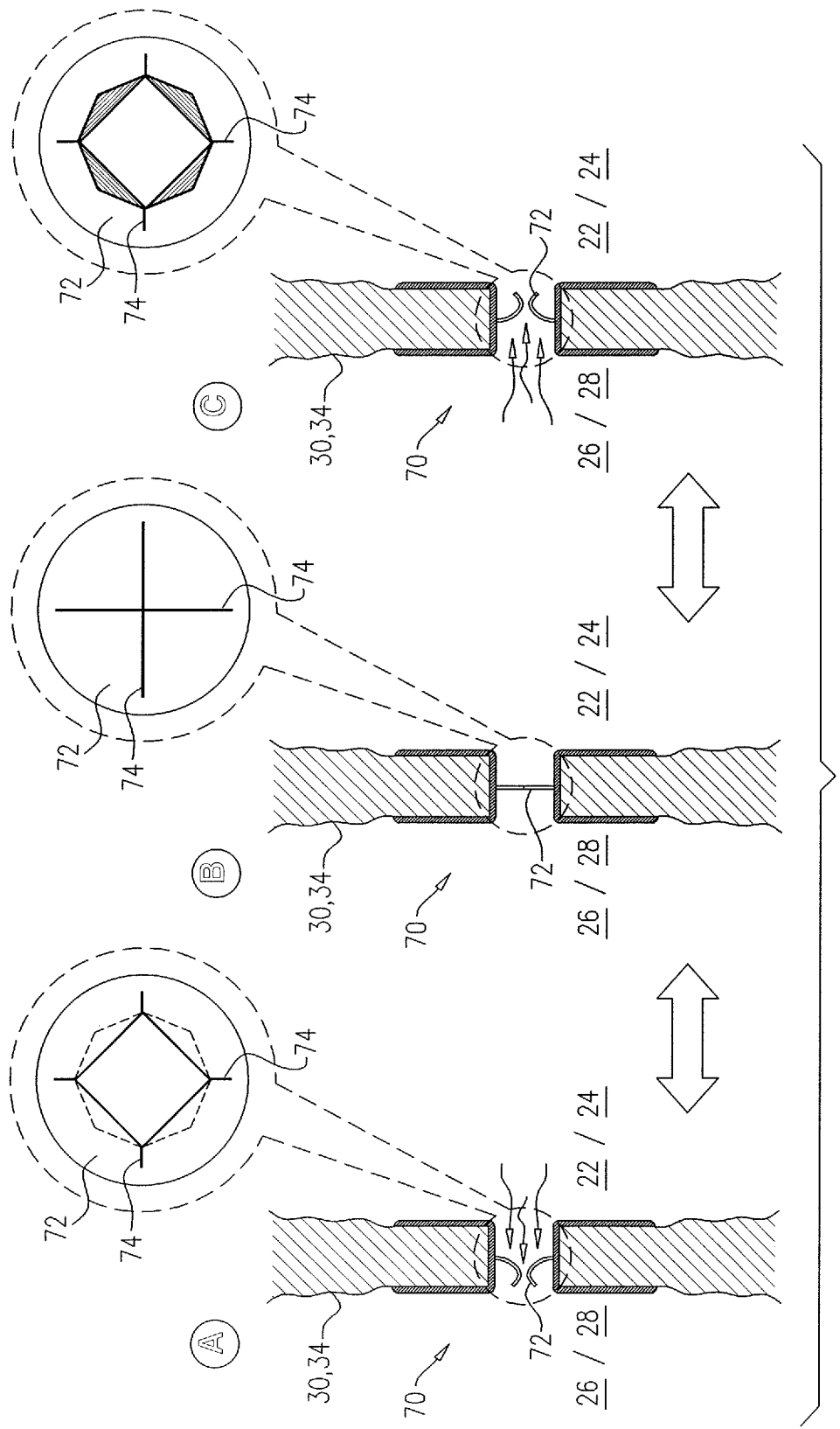

FIG. 5 is a schematic illustration of a septal device 70 that comprises a membrane 72 that regulates blood flow through the lumen. Device 70 is thereby similar to device 60. In contrast to device 60, membrane 72 regulates blood flow but in a bidirectional manner. Membrane 72 opens bidirectionally in response to a blood pressure difference that is greater than a threshold blood pressure difference in either direction. Frame A shows a state of device 70 when blood pressure on the left side of the heart is more than the threshold difference greater than pressure on the right side of the heart. Frame C shows the opposite state. Frame B shows a state of device 70 (i.e., closed, thereby inhibiting blood flow through the lumen of the device) when the blood pressure difference across the device (e.g., across membrane 72) is less than the threshold blood pressure difference. For some applications, the threshold blood pressure difference for device 70 is 4-6 mmHg (e.g., 5 mmHg) (in either direction).

For some applications, membrane 72 is transected by intersecting slits 74, which form the membrane into flaps, which flap open and closed as shown.

Figure 6:
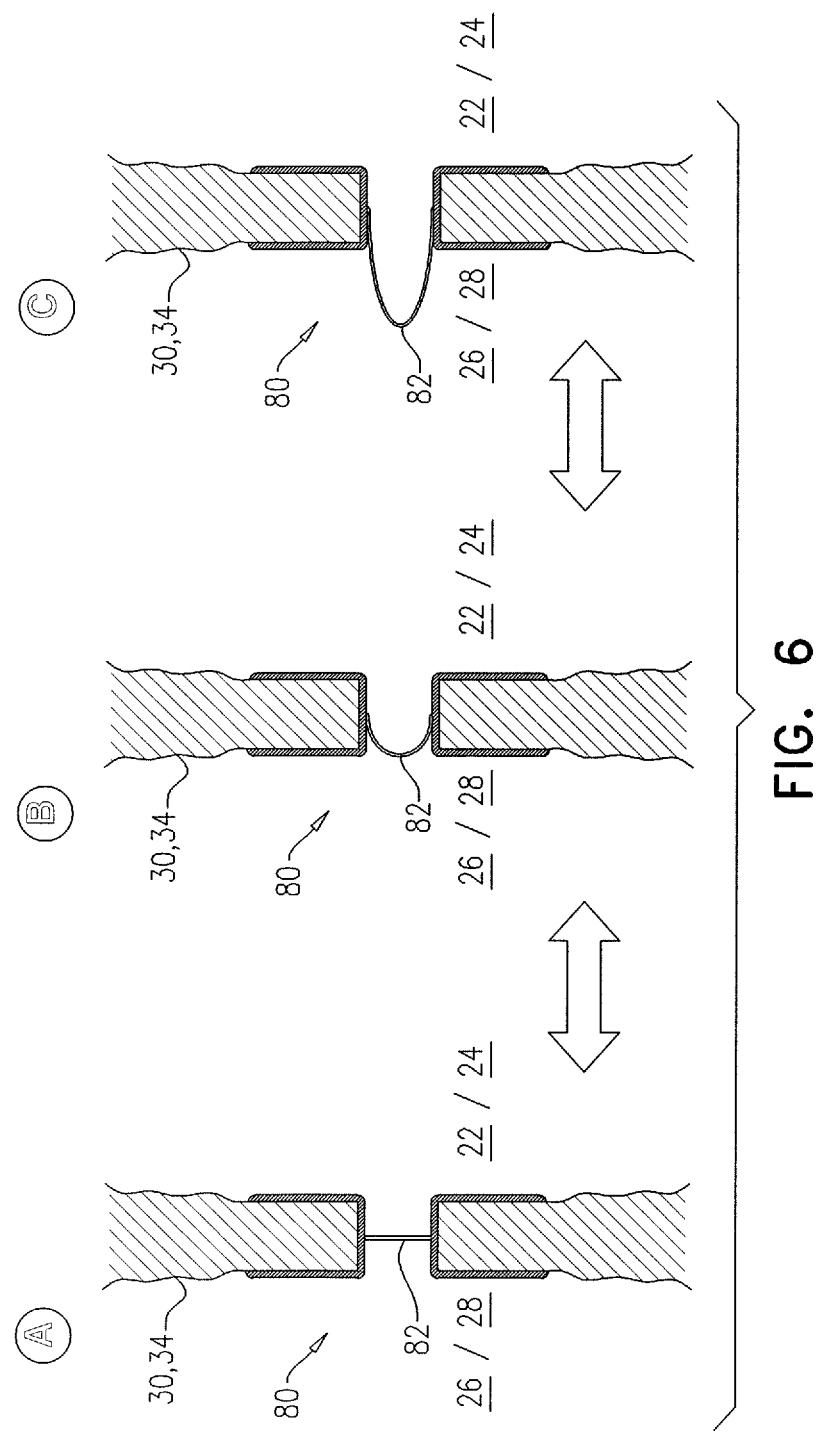
Figure 7:
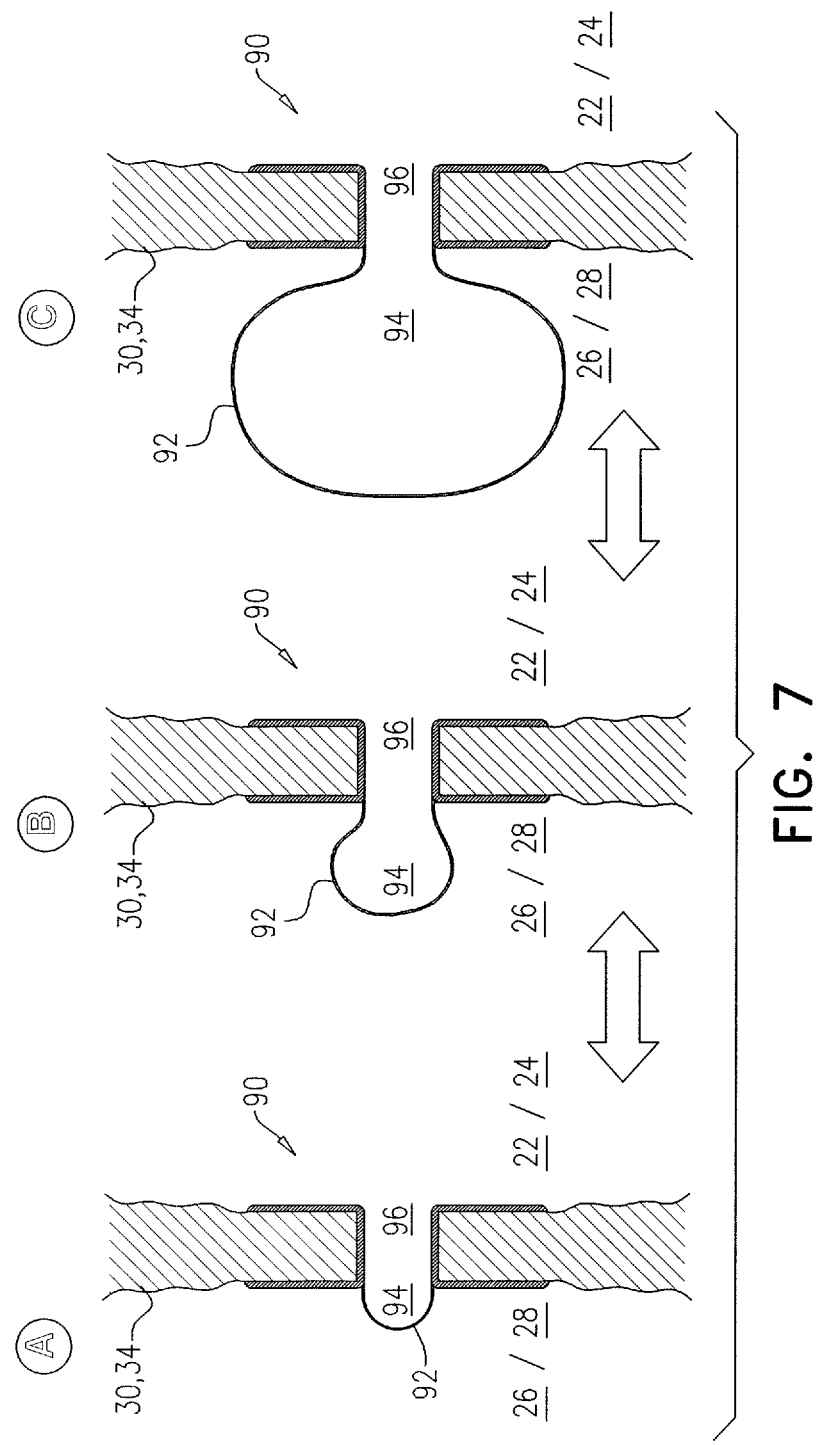

FIGS. 6 and 7 show septal devices 80 and 90, respectively, which also each comprise a membrane. However, the membranes of these devices do not facilitate blood flow between the left and right sides of the heart. Rather, implantation of these devices seals the transseptal fenestration with the membrane.

Device 80 comprises a membrane 82, and device 90 comprises a membrane 92. Membranes 82 and 92 are similar, are both elastic, and both elastically expand (i.e., stretch) in response to a difference in blood pressure across the membrane. Membrane 92 may be considered to be a balloon (e.g., having an interior 94 even in the absence of a pressure difference across the membrane), whereas membrane 82 is generally planar in the absence of a pressure difference across the membrane. Device 90 has an opening 96 into interior 94, and is implanted such that the interior is in fluid communication, via the opening, with the chamber of the left side of the heart. For both FIG. 6 and FIG. 7, frame A shows a state of the device in the absence of a pressure difference across the membrane, frame B shows a state of the device in the presence of a pressure difference across the membrane, and frame C shows a state of the device in the presence of a larger pressure difference across the membrane.

By elastically expanding, membranes 82 and 92 increase the effective volume of the chamber of the left side of the heart, thereby reducing the blood pressure in that chamber without mixing of blood between the left and right sides of the heart.

It is alternatively possible to describe the balloon of device 90, as being a cell that has an interior 94 and an opening 96 into the interior. Device 90 is implanted such that (i) the interior is in fluid communication, via the opening, with a chamber of the left side of the heart, and (ii) a greater blood pressure in the chamber of the left side of the heart relative to a blood pressure in a corresponding chamber of the right side of the heart increases a volume of interior 94 that is disposed within the corresponding chamber of the right side of the heart. This occurs by membrane 92 elastically expanding into the chamber of the right side of the heart in response to this pressure difference.

For some applications, membrane 82 and/or membrane 92 inflate only when blood pressure in the chamber of the left side of the heart is more than 4-6 mmHg (e.g., 5 mmHg) greater than blood pressure in the chamber of the right side of the heart.

The membrane/balloon of devices 80 and 90 may be biased to automatically contract/deflate in response to a reduction of the difference in blood pressure across the fenestration, even if the blood pressure in the chamber of the right side of the heart does not exceed that of the chamber of the left side of the heart.

Figure 8:
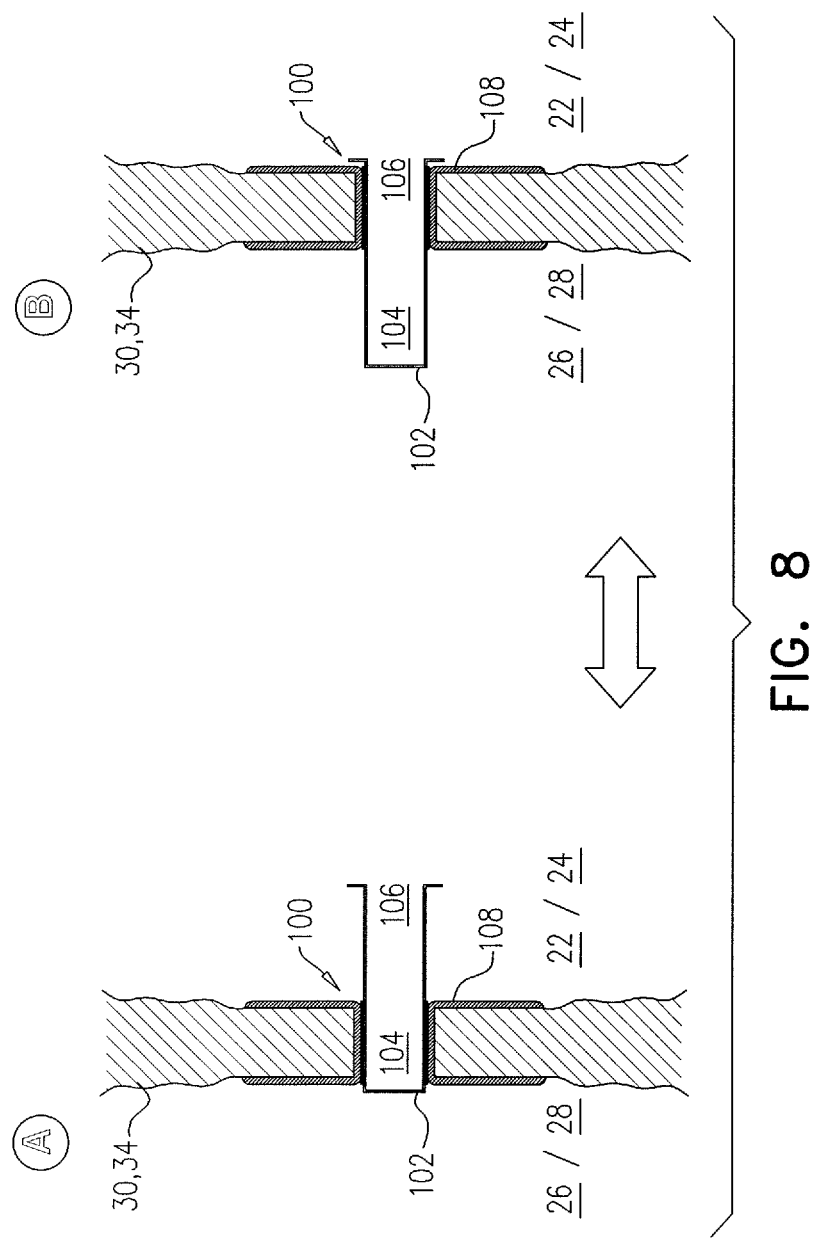

FIG. 8 shows a septal device 100 that comprises a cell 102 that is slidably mounted in a mount 108, such that the mount is fixed at the transseptal fenestration, and the cell slides into the chamber of the right side of the heart in response to the greater blood pressure in the chamber of the left side of the heart. Cell 102 has an interior 104 and an opening 106 into the interior, and is implanted such that the interior is in fluid communication, via the opening, with the chamber of the left side of the heart. Frame A shows the cell not protruding (or protruding minimally) into the chamber of the right side of the heart, and frame B shows the cell having slid into the chamber of the right side of the heart. For some applications, cell 102 is biased (e.g., spring-loaded) to automatically slide out of the chamber of the right side of the heart in response to a reduction of the difference in blood pressure across the fenestration, even if the blood pressure in the chamber of the right side of the heart does not exceed that of the chamber of the left side of the heart.

For some applications, cell 102 slides into the chamber of the right side of the heart only when blood pressure in the chamber of the left side of the heart is more than 4-6 mmHg (e.g., 5 mmHg) greater than blood pressure in the chamber of the right side of the heart.

It is hypothesized by the inventors that the implantation of a septal device described hereinabove in addition to the implantation of prosthetic valve 44 improves a likelihood of a successful long-term outcome of the procedure. For example, the septal devices may facilitate reduction of elevated blood pressure in the right side of the heart, should regurgitation through or around prosthetic valve 44 begin to occur subsequently to implantation of the prosthetic valve. Therefore the implantation of such a septal device may be considered to be prophylactic. For some applications of the invention, the methods described hereinabove are performed on a subject (e.g., an adult subject) who does not suffer from and/or has not been identified (e.g., diagnosed) as suffering from heart failure.

Therefore, a method according to some applications of the invention comprises: (i) making a transseptal fenestration in a heart of a subject (e.g., an adult subject) who has not been identified as suffering from heart failure; (2) advancing a shunt device into the heart; and (3) implanting the shunt device at the transseptal fenestration. Similarly, another method according to some applications of the invention comprises: (1) identifying an adult subject as not suffering from heart failure; and (2) subsequently, making a transseptal fenestration in a heart of the subject.

Reference is now made to FIGS. 9 and 10, which are schematic illustrations of a device 110 and a device 120 implanted in the heart wall, in accordance with an application of the invention. For some applications, devices that reversibly increase the effective volume of the chamber of the left side of the heart are implanted in the heart wall, rather than (as described hereinabove for devices 80, 90 and 100) at a transseptal fenestration. FIG. 9 shows device 110 implanted in the wall of left atrium 22, and FIG. 10 shows device 120 implanted in the wall of left ventricle 24. Devices 110 and 120 may be similar in structure and function (if not dimension) to devices 80, 90 or 100, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a heart of a subject, the method comprising:
    making a transapical puncture into a left ventricle of the heart;
    making a transseptal fenestration in the heart via the transapical puncture;
    delivering a prosthetic valve via the transapical puncture and implanting the prosthetic valve at a mitral valve of the heart; and subsequently to delivering the prosthetic valve and making the transseptal fenestration, closing the transapical puncture.

2. The method according to claim 1, wherein the subject has not been identified as suffering from heart failure, and wherein performing the method comprises performing the method on the subject that has not been identified as suffering from heart failure.

3. The method according to claim 1, wherein making the transseptal fenestration comprises making a fenestration in the interventricular septum.

4. The method according to claim 1, wherein making the transseptal fenestration comprises making a fenestration in the interatrial septum.

5. The method according to claim 1, wherein making the transseptal fenestration comprises making the transseptal fenestration after implanting the prosthetic valve.

6. The method according to claim 1, wherein making the transseptal fenestration comprises making the transseptal fenestration before implanting the prosthetic valve.

7. The method according claim 1, further comprising advancing a distal end of a tube through the transapical puncture, and wherein delivering the prosthetic valve via the transapical puncture comprises delivering the prosthetic valve via the tube.

8. The method according to claim 7, wherein making the transseptal fenestration comprises making the transseptal fenestration via the tube.

9. The method according to claim 1, further comprising implanting a shunt device into the transseptal fenestration.

10. The method according to claim 9, wherein the shunt device includes a check valve, and implanting the shunt device comprises implanting the shunt device such that the check valve facilitates one-way blood flow from a chamber of the left side of the heart, via the transseptal fenestration, to a chamber of the right side of the heart.

11. The method according to claim 9, wherein implanting the shunt device comprises implanting a shunt device that is shaped to define a lumen, and includes a membrane that regulates blood flow through the lumen.

12. The method according to claim 11, wherein implanting the shunt device comprises implanting a shunt device that includes a membrane that (a) has (i) a closed position in which the membrane inhibits blood flow through the lumen, and (ii) an open position in which the inhibiting of the blood flow is reduced, resides in the closed position while a blood pressure difference across the membrane is lower than a threshold blood pressure difference of 4-6 mmHg (e.g., 5 mmHg), and moves from the closed position into the open position in response to the blood pressure difference exceeding the threshold blood pressure difference.

13. The method according to claim 12, wherein the membrane moves from the closed position into the open position in response to the blood pressure difference exceeding the threshold blood pressure difference in either direction across the membrane, and implanting the shunt device that includes the membrane comprises implanting the shunt device that includes the membrane that moves from the closed position into the open position in response to the blood pressure difference exceeding the threshold blood pressure difference in either direction across the membrane.

14. The method according to claim 11, wherein the membrane is transected by intersecting slits, and implanting the shunt device comprises implanting the shunt device that includes the membrane that is transected by intersecting slits.

15. The method according to claim 1, further comprising implanting at the transseptal fenestration, a balloon device that includes a balloon having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart inflates the balloon such that the balloon reversibly expands into the corresponding chamber of the right side of the heart.

16. The method according to claim 15, wherein the balloon is elastic, and implanting the balloon device comprises implanting the balloon device such that the balloon automatically deflates in response to a reduction in the greater blood pressure in the chamber of the left side of the heart.

17. The method according to claim 15, wherein implanting the balloon device comprises implanting the balloon such that the balloon inflates only when blood pressure in the chamber of the left side of the heart is more than 4-6 mmHg greater than blood pressure in the chamber of the right side of the heart.

18. The method according to claim 15, wherein implanting the balloon device comprises sealing the transseptal fenestration with the balloon device.

19. The method according to claim 1, further comprising implanting at the transseptal fenestration, an elastic membrane that elastically expands in response to a difference in blood pressure across the membrane.

20. The method according to claim 19, wherein implanting the elastic membrane comprises sealing the transseptal fenestration with the elastic membrane.

21. The method according to claim 1, further comprising implanting at the transseptal fenestration, a cell having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart increases a volume of the interior that is disposed within the corresponding chamber of the right side of the heart.

22. The method according to claim 21, wherein the cell includes an elastic membrane, and implanting the cell comprises implanting the cell that includes the elastic membrane, such that the elastic membrane elastically expands into the chamber of the right side of the heart in response to the greater blood pressure in the chamber of the left side of the heart.

23. The method according to claim 21, wherein the cell is a balloon, and implanting the cell comprises implanting the balloon, such that the balloon expands into the chamber of the right side of the heart in response to the greater blood pressure in the chamber of the left side of the heart.

24. The method according to claim 21, wherein implanting the cell comprises implanting a cell that is slidably mounted in a mount, such that the mount is fixed at the transseptal fenestration, and the cell slides into the chamber of the right side of the heart in response to the greater blood pressure in the chamber of the left side of the heart.

25. The method according to claim 21, wherein implanting the cell comprises implanting the cell such that the volume of the interior that is disposed within the corresponding chamber of the right side of the heart increases only when the blood pressure in the chamber of the left side of the heart is greater than the blood pressure in the chamber of the right side of the heart by more than a threshold difference of 4-6 mmHg.

26. A method for use with a heart of a subject, the method comprising:
   making a transapical puncture into a left ventricle of the heart;
   making a transseptal fenestration in the heart in the interventricular septum;
   delivering a prosthetic valve via the transapical puncture and implanting the prosthetic valve at a mitral valve of the heart; and
   subsequently to delivering the prosthetic valve and making the transseptal fenestration, closing the transapical puncture.

27. The method according to claim 26, wherein the subject has not been identified as suffering from heart failure, and wherein performing the method comprises performing the method on the subject that has not been identified as suffering from heart failure.

28. The method according to claim 26, wherein making the transseptal fenestration comprises making the transseptal fenestration via the transapical puncture.

29. The method according to claim 26, wherein making the transseptal fenestration comprises making the transseptal fenestration via a transfemoral route.

30. The method according to claim 26, wherein making the transseptal fenestration comprises making the transseptal fenestration after implanting the prosthetic valve.

31. The method according to claim 26, wherein making the transseptal fenestration comprises making the transseptal fenestration before implanting the prosthetic valve.

32. The method according claim 26, further comprising advancing a distal end of a tube through the transapical puncture, and wherein delivering the prosthetic valve via the transapical puncture comprises delivering the prosthetic valve via the tube.

33. The method according to claim 32, wherein making the transseptal fenestration comprises making the transseptal fenestration via the tube.

34. The method according to claim 26, further comprising implanting a shunt device into the transseptal fenestration.

35. The method according to claim 34, wherein the shunt device includes a check valve, and implanting the shunt device comprises implanting the shunt device such that the check valve facilitates one-way blood flow from a chamber of the left side of the heart, via the transseptal fenestration, to a chamber of the right side of the heart.

36. The method according to claim 34, wherein implanting the shunt device comprises implanting a shunt device that is shaped to define a lumen, and includes a membrane that regulates blood flow through the lumen.

37. The method according to claim 36, wherein implanting the shunt device comprises implanting a shunt device that includes a membrane that (a) has (i) a closed position in which the membrane inhibits blood flow through the lumen, and (ii) an open position in which the inhibiting of the blood flow is reduced, resides in the closed position while a blood pressure difference across the membrane is lower than a threshold blood pressure difference of 4-6 mmHg (e.g., 5 mmHg), and moves from the closed position into the open position in response to the blood pressure difference exceeding the threshold blood pressure difference.

38. The method according to claim 37, wherein the membrane moves from the closed position into the open position in response to the blood pressure difference exceeding the threshold blood pressure difference in either direction across the membrane, and implanting the shunt device that includes the membrane comprises implanting the shunt device that includes the membrane that moves from the closed position into the open position in response to the blood pressure difference exceeding the threshold blood pressure difference in either direction across the membrane.

39. The method according to claim 36, wherein the membrane is transected by intersecting slits, and implanting the shunt device comprises implanting the shunt device that includes the membrane that is transected by intersecting slits.

40. The method according to claim 26, further comprising implanting at the transseptal fenestration, a balloon device that includes a balloon having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart inflates the balloon such that the balloon reversibly expands into the corresponding chamber of the right side of the heart.

41. The method according to claim 40, wherein the balloon is elastic, and implanting the balloon device comprises implanting the balloon device such that the balloon automatically deflates in response to a reduction in the greater blood pressure in the chamber of the left side of the heart.

42. The method according to claim 40, wherein implanting the balloon device comprises implanting the balloon such that the balloon inflates only when blood pressure in the chamber of the left side of the heart is more than 4-6 mmHg greater than blood pressure in the chamber of the right side of the heart.

43. The method according to claim 40, wherein implanting the balloon device comprises sealing the transseptal fenestration with the balloon device.

44. The method according to claim 26, further comprising implanting at the transseptal fenestration, an elastic membrane that elastically expands in response to a difference in blood pressure across the membrane.

45. The method according to claim 44, wherein implanting the elastic membrane comprises sealing the transseptal fenestration with the elastic membrane.

46. The method according to claim 26, further comprising implanting at the transseptal fenestration, a cell having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart increases a volume of the interior that is disposed within the corresponding chamber of the right side of the heart.

47. The method according to claim 46, wherein the cell includes an elastic membrane, and implanting the cell comprises implanting the cell that includes the elastic membrane, such that the elastic membrane elastically expands into the chamber of the right side of the heart in response to the greater blood pressure in the chamber of the left side of the heart.

48. The method according to claim 46, wherein the cell is a balloon, and implanting the cell comprises implanting the balloon, such that the balloon expands into the chamber of the right side of the heart in response to the greater blood pressure in the chamber of the left side of the heart.

49. The method according to claim 46, wherein implanting the cell comprises implanting a cell that is slidably mounted in a mount, such that the mount is fixed at the transseptal fenestration, and the cell slides into the chamber of the right side of the heart in response to the greater blood pressure in the chamber of the left side of the heart.

50. The method according to claim 46, wherein implanting the cell comprises implanting the cell such that the volume of the interior that is disposed within the corresponding chamber of the right side of the heart increases only when the blood pressure in the chamber of the left side of the heart is greater than the blood pressure in the chamber of the right side of the heart by more than a threshold difference of 4-6 mmHg.

51. A method for use with a heart of a subject, the method comprising:
    making a transapical puncture into a left ventricle of the heart;
    delivering a prosthetic valve via the transapical puncture and implanting the prosthetic valve at a mitral valve of the heart;
    subsequently to implanting the prosthetic valve, making a transseptal fenestration in the heart; and
    subsequently to making the transseptal fenestration, closing the transapical puncture.

52. The method according to claim 51, wherein the subject has not been identified as suffering from heart failure, and wherein performing the method comprises performing the method on the subject that has not been identified as suffering from heart failure.

53. The method according to claim 51, wherein making the transseptal fenestration comprises making the transseptal fenestration via the transapical puncture.

54. The method according to claim 51, wherein making the transseptal fenestration comprises making the transseptal fenestration via a transfemoral route.

55. The method according to claim 51, wherein making the transseptal fenestration comprises making a fenestration in the interventricular septum.

56. The method according to claim 51, wherein making the transseptal fenestration comprises making a fenestration in the interatrial septum.

57. The method according claim 51, further comprising advancing a distal end of a tube through the transapical puncture, and wherein delivering the prosthetic valve via the transapical puncture comprises delivering the prosthetic valve via the tube.

58. The method according to claim 57, wherein making the transseptal fenestration comprises making the transseptal fenestration via the tube.

59. The method according to claim 51, further comprising implanting a shunt device into the transseptal fenestration.

60. The method according to claim 59, wherein the shunt device includes a check valve, and implanting the shunt device comprises implanting the shunt device such that the check valve facilitates one-way blood flow from a chamber of the left side of the heart, via the transseptal fenestration, to a chamber of the right side of the heart.

61. The method according to claim 59, wherein implanting the shunt device comprises implanting a shunt device that is shaped to define a lumen, and includes a membrane that regulates blood flow through the lumen.

62. The method according to claim 61, wherein implanting the shunt device comprises implanting a shunt device that includes a membrane that (a) has (i) a closed position in which the membrane inhibits blood flow through the lumen, and (ii) an open position in which the inhibiting of the blood flow is reduced, resides in the closed position while a blood pressure difference across the membrane is lower than a threshold blood pressure difference of 4-6 mmHg (e.g., 5 mmHg), and moves from the closed position into the open position in response to the blood pressure difference exceeding the threshold blood pressure difference.

63. The method according to claim 62, wherein the membrane moves from the closed position into the open position in response to the blood pressure difference exceeding the threshold blood pressure difference in either direction across the membrane, and implanting the shunt device that includes the membrane comprises implanting the shunt device that includes the membrane that moves from the closed position into the open position in response to the blood pressure difference exceeding the threshold blood pressure difference in either direction across the membrane.

64. The method according to claim 61, wherein the membrane is transected by intersecting slits, and implanting the shunt device comprises implanting the shunt device that includes the membrane that is transected by intersecting slits.

65. The method according to claim 51, further comprising implanting at the transseptal fenestration, a balloon device that includes a balloon having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart inflates the balloon such that the balloon reversibly expands into the corresponding chamber of the right side of the heart.

66. The method according to claim 65, wherein the balloon is elastic, and implanting the balloon device comprises implanting the balloon device such that the balloon automatically deflates in response to a reduction in the greater blood pressure in the chamber of the left side of the heart.

67. The method according to claim 65, wherein implanting the balloon device comprises implanting the balloon such that the balloon inflates only when blood pressure in the chamber of the left side of the heart is more than 4-6 mmHg greater than blood pressure in the chamber of the right side of the heart.

68. The method according to claim 65, wherein implanting the balloon device comprises sealing the transseptal fenestration with the balloon device.

69. The method according to claim 51, further comprising implanting at the transseptal fenestration, an elastic membrane that elastically expands in response to a difference in blood pressure across the membrane.

70. The method according to claim 69, wherein implanting the elastic membrane comprises sealing the transseptal fenestration with the elastic membrane.

71. The method according to claim 51, further comprising implanting at the transseptal fenestration, a cell having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart increases a volume of the interior that is disposed within the corresponding chamber of the right side of the heart.

72. The method according to claim 71, wherein the cell includes an elastic membrane, and implanting the cell comprises implanting the cell that includes the elastic membrane, such that the elastic membrane elastically expands into the chamber of the right side of the heart in response to the greater blood pressure in the chamber of the left side of the heart.

73. The method according to claim 71, wherein the cell is a balloon, and implanting the cell comprises implanting the balloon, such that the balloon expands into the chamber of the right side of the heart in response to the greater blood pressure in the chamber of the left side of the heart.

74. The method according to claim 71, wherein implanting the cell comprises implanting a cell that is slidably mounted in a mount, such that the mount is fixed at the transseptal fenestration, and the cell slides into the chamber of the right side of the heart in response to the greater blood pressure in the chamber of the left side of the heart.

75. The method according to claim 71, wherein implanting the cell comprises implanting the cell such that the volume of the interior that is disposed within the corresponding chamber of the right side of the heart increases only when the blood pressure in the chamber of the left side of the heart is greater than the blood pressure in the chamber of the right side of the heart by more than a threshold difference of 4-6 mmHg.

76. A method for use with a heart of a subject, the method comprising:
  making a transapical puncture into a left ventricle of the heart;
  making a transseptal fenestration in the heart;
  advancing a distal end of a tube through the transapical puncture;
  delivering a prosthetic valve via the tube disposed through the transapical puncture and implanting the prosthetic valve at a mitral valve of the heart; and
  subsequently to delivering the prosthetic valve and making the transseptal fenestration, closing the transapical puncture.

77. The method according to claim 76, wherein the subject has not been identified as suffering from heart failure, and wherein performing the method comprises performing the method on the subject that has not been identified as suffering from heart failure.

78. The method according to claim 76, wherein making the transseptal fenestration comprises making the transseptal fenestration via the transapical puncture.

79. The method according to claim 76, wherein making the transseptal fenestration comprises making the transseptal fenestration via a transfemoral route.

80. The method according to claim 76, wherein making the transseptal fenestration comprises making a fenestration in the interventricular septum.

81. The method according to claim 76, wherein making the transseptal fenestration comprises making a fenestration in the interatrial septum.

82. The method according to claim 76, wherein making the transseptal fenestration comprises making the transseptal fenestration after implanting the prosthetic valve.

83. The method according to claim 76, wherein making the transseptal fenestration comprises making the transseptal fenestration before implanting the prosthetic valve.

84. The method according to claim 76, wherein making the transseptal fenestration comprises making the transseptal fenestration via the tube.

85. The method according to claim 76, further comprising implanting a shunt device into the transseptal fenestration.

86. The method according to claim 85, wherein the shunt device includes a check valve, and implanting the shunt device comprises implanting the shunt device such that the check valve facilitates one-way blood flow from a chamber of the left side of the heart, via the transseptal fenestration, to a chamber of the right side of the heart.

87. The method according to claim 85, wherein implanting the shunt device comprises implanting a shunt device that is shaped to define a lumen, and includes a membrane that regulates blood flow through the lumen.

88. The method according to claim 87, wherein implanting the shunt device comprises implanting a shunt device that includes a membrane that (a) has (i) a closed position in which the membrane inhibits blood flow through the lumen, and (ii) an open position in which the inhibiting of the blood flow is reduced, resides in the closed position while a blood pressure difference across the membrane is lower than a threshold blood pressure difference of 4-6 mmHg (e.g., 5 mmHg), and moves from the closed position into the open position in response to the blood pressure difference exceeding the threshold blood pressure difference.

89. The method according to claim 88, wherein the membrane moves from the closed position into the open position in response to the blood pressure difference exceeding the threshold blood pressure difference in either direction across the membrane, and implanting the shunt device that includes the membrane comprises implanting the shunt device that includes the membrane that moves from the closed position into the open position in response to the blood pressure difference exceeding the threshold blood pressure difference in either direction across the membrane.

90. The method according to claim 11, wherein the membrane is transected by intersecting slits, and implanting the shunt device comprises implanting the shunt device that includes the membrane that is transected by intersecting slits.

91. The method according to claim 76, further comprising implanting at the transseptal fenestration, a balloon device that includes a balloon having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart inflates the balloon such that the balloon reversibly expands into the corresponding chamber of the right side of the heart.

92. The method according to claim 91, wherein the balloon is elastic, and implanting the balloon device comprises implanting the balloon device such that the balloon automatically deflates in response to a reduction in the greater blood pressure in the chamber of the left side of the heart.

93. The method according to claim 91, wherein implanting the balloon device comprises implanting the balloon such that the balloon inflates only when blood pressure in the chamber of the left side of the heart is more than 4-6 mmHg greater than blood pressure in the chamber of the right side of the heart.

94. The method according to claim 91, wherein implanting the balloon device comprises sealing the transseptal fenestration with the balloon device.

95. The method according to claim 76, further comprising implanting at the transseptal fenestration, an elastic membrane that elastically expands in response to a difference in blood pressure across the membrane.

96. The method according to claim 95, wherein implanting the elastic membrane comprises sealing the transseptal fenestration with the elastic membrane.

97. The method according to claim 76, further comprising implanting at the transseptal fenestration, a cell having an interior and an opening into the interior, such that (i) the interior is in fluid communication, via the opening, with a chamber of the left side of the heart, and (ii) a greater blood pressure in the chamber of the left side of the heart relative to a blood pressure in a corresponding chamber of the right side of the heart increases a volume of the interior that is disposed within the corresponding chamber of the right side of the heart.

98. The method according to claim 97, wherein the cell includes an elastic membrane, and implanting the cell comprises implanting the cell that includes the elastic membrane, such that the elastic membrane elastically expands into the chamber of the right side of the heart in response to the greater blood pressure in the chamber of the left side of the heart.

99. The method according to claim 97, wherein the cell is a balloon, and implanting the cell comprises implanting the balloon, such that the balloon expands into the chamber of the right side of the heart in response to the greater blood pressure in the chamber of the left side of the heart.

100. The method according to claim 97, wherein implanting the cell comprises implanting a cell that is slidably mounted in a mount, such that the mount is fixed at the transseptal fenestration, and the cell slides into the chamber of the right side of the heart in response to the greater blood pressure in the chamber of the left side of the heart.

101. The method according to claim 97, wherein implanting the cell comprises implanting the cell such that the volume of the interior that is disposed within the corresponding chamber of the right side of the heart increases only when the blood pressure in the chamber of the left side of the heart is greater than the blood pressure in the chamber of the right side of the heart by more than a threshold difference of 4-6 mmHg.

\* \* \* \* \*